United States Patent [19]
Suetsugu et al.

[11] Patent Number: 5,690,914
[45] Date of Patent: Nov. 25, 1997

[54] EXTERNAL PREPARATION FOR SKIN

[75] Inventors: Masaru Suetsugu; Manami Ohnuma; Yoshihiro Morikawa; Yuki Yamase; Naoe Akiyama; Kenji Kitamura, all of Yokohama, Japan

[73] Assignee: Shiseido Co., Ltd, Tokyo, Japan

[21] Appl. No.: 112,797

[22] Filed: Aug. 27, 1993

[30] Foreign Application Priority Data

| Aug. 27, 1992 | [JP] | Japan | 4-252324 |
|---|---|---|---|
| Aug. 27, 1992 | [JP] | Japan | 4-252325 |
| Aug. 31, 1992 | [JP] | Japan | 4-255822 |
| Aug. 31, 1992 | [JP] | Japan | 4-255823 |
| Aug. 31, 1992 | [JP] | Japan | 4-255824 |
| Sep. 1, 1992 | [JP] | Japan | 4-257348 |
| Sep. 1, 1992 | [JP] | Japan | 4-257349 |
| Sep. 1, 1992 | [JP] | Japan | 4-257350 |
| Sep. 1, 1992 | [JP] | Japan | 4-257351 |

[51] Int. Cl.$^6$ .............. A61K 7/42; A61K 7/44; A61K 7/135
[52] U.S. Cl. .............. 424/59; 424/60; 424/62; 424/63; 514/844
[58] Field of Search .............. 424/59, 62, 60, 424/63; 514/844

[56] References Cited

U.S. PATENT DOCUMENTS

4,600,583  7/1986  Stevens et al. ............ 424/91

FOREIGN PATENT DOCUMENTS

| A0041826 | 6/1981 | European Pat. Off. . |
| A2498183 | 7/1982 | France . |
| 57-21360 | 2/1982 | Japan . |
| 1-93519 | 4/1982 | Japan . |
| 57-59847 | 4/1982 | Japan . |
| 57-59848 | 4/1982 | Japan . |
| 57-59852 | 4/1982 | Japan . |
| 57-126461 | 8/1982 | Japan . |
| 4-210611 | 7/1992 | Japan . |

OTHER PUBLICATIONS

CA 107 : 168406, 1987.
CA 116 : 241730, 1992.
Journal of Medicinal Chemistry; vol. 15, No. 3, Mar. 1972; pp. 247–255; "Medicinal Chemical Studies on Antiplasmin Drugs. 4. Chemical Modification of trans–4–Aminomethylcyclohexanecarboxylic Acid and Its Effects On Antiplasmin Activity"; A. Okano, et al.
Journal of the American Chemical Society; vol. 74; 1952; pp. 676–678; The Preparation of Peptides Using Mixed Carbonic-carboxylic Acid Anhydrides; J. R. Vaughan, Jr., et al.
Journal of the American Chemical Society; vol. 86, No. 9, May 5, 1964; pp. 1839–1842; The Use of Esters of N–Hydroxysuccinimide in Peptide Synthesis; George W. Anderson, et al.
Journal of the American Chemical Society; vol. 89; 1967; pp. 5012–5017; A Reinvestigation of the Mixed Carbonic Anhydride Method of Peptide Synthesis; George W. Anderson, et al.

*Primary Examiner*—Shean C. Wu
*Attorney, Agent, or Firm*—Townsend & Banta

[57] ABSTRACT

An external preparation for skin including one or more than two types of tranexamic acid derivatives represented by the following general formula (A). GENERAL FORMULA (A)

$$\underset{R_3}{\overset{R_2}{\diagdown}} N H_2 C - \hspace{-2pt}\bigcirc\hspace{-2pt} - \overset{O}{\overset{\|}{C}} - R_1 \quad (A)$$

(In the formula (A), $R_1$, $R_2$ and $R_3$ represents hydrogen atoms or substituents and at least one of these is the substituent.) The external preparation for skin including the derivatives have excellent depigmentation effect as well as skin care effect.

10 Claims, No Drawings

EXTERNAL PREPARATION FOR SKIN

FIELD OF THE INVENTION

The present invention relates to an external preparation for skin, and more particularly to a remarkably improved skin depigmentation agent thereof.

BACKGROUND ART

Although the mechanisms of pigmentation such as melasma. chloasma and the like in the skin are not fully understood, it is believed that a melanin pigment is formed and abnormally deposited in the skin due to a hormone abnormality and UV light irritation caused by sunlight. The above-mentioned pigmentation is generally treated by administering substances suppressing the formation of melanin. For example, Vitamin C is administered in a large amount: glutathione or a similar compound is injected; or L-ascorbic acid, kojic acid, cysteine, or a similar compound is applied to localized areas in the form of an ointment, cream, or lotion.

On the other hand, in the United Sates and Europe, hydroquinine preparations are used as pharmaceuticals.

However, the depigmentation effects of the above-mentioned compounds, except for hydroquinone, are very weak. Furthermore, although the depigmentation effects of hydroquinone on the skin are apparently recognized, the use of hydroquinone on the skin is generally limited due to its contact allergenicity.

DISCLOSURE OF THE INVENTION

Accordingly, it is an object of the present invention to eliminate the above-described problems of the prior art and to provide an external preparation for skin which has excellent depigmentation effect and high safety.

As a result of studies undertaken by the present inventors so as to attain this aim, it has been found that certain types of tranexamic acid derivatives had suppression effect of melanine generation and excellent depigmentation effect to improve the depigmentation in the skin and skin trouble. The present invention has been achieved on the basis of these findings.

In the first aspect of the present invention, there is provided an external preparation for skin including one or more than two types of tranexamic acid derivatives represented by the following general formula (A).

GENERAL FORMULA (A)

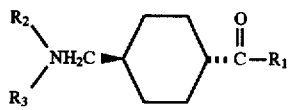
(A)

In the general formula (A), $R_1$, $R_2$, and R3 represent hydrogen atom or substituents and at least one of these is the substituent.

In the first aspect of the present invention, there is provided an external preparation for skin including one or more than two types of amide derivatives of tranexamic acid and the salts thereof represented by the following general formula (B).

GENERAL FORMULA (B)

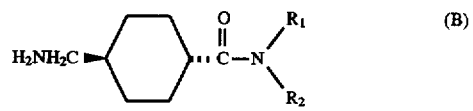
(B)

In the formula (B), $R_1$ and $R_2$ are the same or different from each other and represent a hydrogen atom, normal chain or branched alkyl group having 1–18 carbon atoms, a cycloalkyl group having 5–8 carbon atoms, benzyl group or residues having the following general formula (C). As shown in (C), X represents a lower alkyl group, a lower alkoxy group, a hydroxy group, an amino group or a halogen atom, where n=0–3).

GENERAL FORMULA (C)

(C)

In the third aspect of the present invention, there is provided an external preparation for the skin including one or more than two types of amide derivatives of tranexamic acid and the salts thereof represented by the following general formula (D).

GENERAL FORMULA (D)

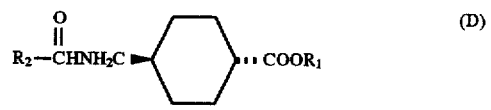
(D)

In the formula (D), $R_1$ represents a hydrogen atom or a lower alkyl. $R_2$ represents an alkyl group, a cycloalkyl group, an alkyl group, a cycloalkenyl group, a pyridyl group, or a trifluoromethyl group. In the following general formula (E), X and Y represent a hydroxy group, alkoxy group, amino group or halogen atom, respectively where m=0–3 and n=0–3). In the following general formula (F), Z represents a hydroxyl group or a lower alkoxy group where j=0–3.

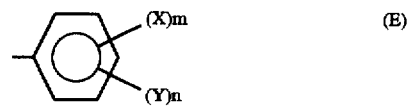
(E)

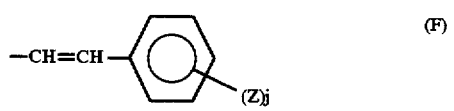
(F)

In the forth aspect of the present invention, there is provided an external preparation for skin including one or more than two types of tranexamic acid derivatives and the salts thereof represented by the following general formula (G).

GENERAL FORMULA (G)

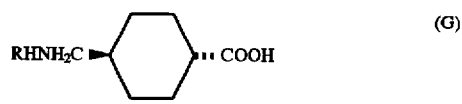
(G)

In the formula (G), R represents an amino acid residue.

In the fifth aspect of the present invention, there is provided an external preparation for skin including one or more than two types of tranexamic acid derivatives and the salts thereof represented by the following general formula (H).

GENERAL FORMULA (H)

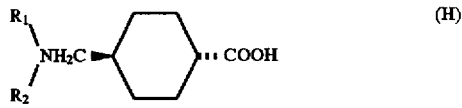

In the formula (H), $R_1$ and $R_2$ are same or different from each other and represent a hydrogen atom or normal chain or branched alkyl group having 1–4 carbon atoms. Both of the $R_1$ and $R_2$ can not be hydrogen atom.

In the sixth aspect of the present invention, there is provided an external preparation for skin including one or more than two types of tranexamic acid derivatives and the salts thereof represented by the following general formula (I).

GENERAL FORMULA (I)

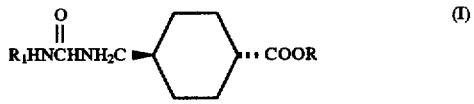

In the formula (I), R represents a hydrogen atom or a lower alkyl group, $R_1$ represents a hydrogen atom, an alkyl group, a cycloalkyl group, an aryl group, an aralkyl or —(CH$_2$)$_n$COOR$_2$, $R_2$ represents a hydrogen atom or a lower alkyl group and n=1–8.

In the seventh aspect of the present invention, there is provided an external preparation for skin including one or more than two types of cyclohexanecarboxylic acid derivatives and the salts thereof represented by the following general formula (J).

GENERAL FORMULA (J)

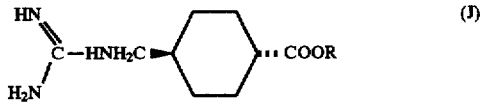

In the formula (J), R represents a hydrogen atom, a normal chain, branched chain or cyclic alkyl group or an aralkyl group.

In the eighth aspect of the present invention, there is provided an external preparation for skin including one or more than two types of trans-4-guanidinomethylcyclohexanecarboxylic acid derivatives represented by the following general formula (K).

GENERAL FORMULA (K)

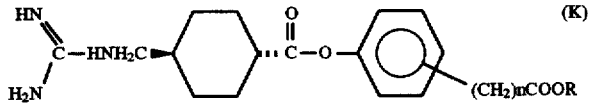

In the formula (K), R represents a hydrogen atom, a lower alkyl group, a benzyl group, or a phenyl where n=0–2.

In the nineth aspect of the present invention, there is provided an external preparation for the skin including one or more than two types of trans-4-guanidinomethylcyclohexanecarboxylic acid derivatives and the salts thereof represented by the following general formula (L).

GENERAL FORMULA (L)

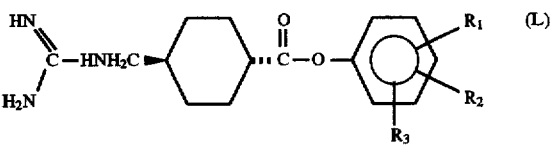

In the formula (L), $R_1$, $R_2$ and $R_3$ are same or different from each other and represent a hydrogen atom, lower alkyl group, lower alkoxy group, alkanoyl group, phenyl group, halogen atom, trihalogenomethyl group, nitro group, acetoamino group, carbamoyl group, sulfamoyl group, benzoyl group, phenoxy group, benzyloxy group, formyl group or cyano group.

In the tenth aspect of the present invention, there is provided an external preparation for the skin including one or more than two types of tranexamic acid derivatives and the salts thereof represented by the following general formula (M).

GENERAL FORMULA (M)

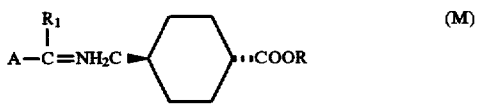

In general formula (M), A represents a phenyl group, a pyridyl group, a p-isopropenylphenyl group or the residue represented by the following general formula (N).

GENERAL FORMULA (N)

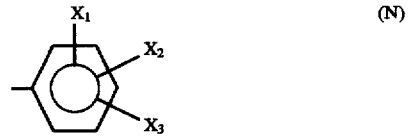

In formula (N), $X_1$ represents a hydrogen atom, a hydroxy group or a methoxy group. $X_2$ represents a hydrogen atom, a hydroxy group or a methoxy group. $X_3$ represents a hydroxy group, a methoxy group, a halogen atom, a nitro group, a trifluoromethyl group, a carboxyl group or the following general formula (O).

GENERAL FORMULA (O)

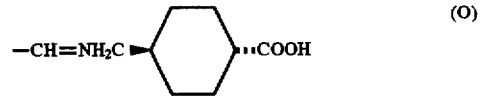

R represents a hydrogen atom, Na or an alkyl group having from 1–4 of carbon atoms. $R_1$ represents a hydrogen atom or an alkyl group having from 1–10 of carbon atoms.

The composition of the present invention is explained in detail hereinafter.

COMPOUND GROUP 1

General Formula (B)

It is possible to synthesize the amide derivatives and the salt of tranexamic acid according to the present invention by the method described in, for example, Acta Pharm. Suecica. 7, 441 (1970). J. Med. Chem., 15, 247 (1972).

Namely, the amino group of the tranexamic acid is protected by the suitable protecting group such as, for example, benzyloxycarbonyl group. After that, an amine ingredient reacts with the protected derivatives or a reactive protected derivatives thereof. As a result, amide derivatives of the protected tranexamic acid can be obtained. As an example of the reactive protected derivatives, acyl halides such as acid chloride and bromides, or mixed acid anhydrides can be cited. After the reaction, the amide derivatives of tranexamic acid can be synthesized by removing the protecting group by, for example, catalytic reduction.

The above-described compound can be in forms of an inorganic acid salts such as salts of hydrochloric acid, sulfuric acid, phosphoric acid and hydrobromic acid or organic acid salts such as a salt of acetic acid, lactic acid, maleic acid, fumaric acid, tartaric acid, citric acid, methanesulfonic acid, and p-toluene sulfonic acid.

Preferable examples of the compound group 1 are: Trans-4-aminomethylcyclohexanecarboxamide, Trans-4-aminomethylcyclohexanecarboxamide hydrochloride, N-n-hexyl-trans-4-aminomethylcyclohexanecarboxamide, N-n-hexyl-trans-4-aminomethylcyclohexanecarboxamide hydrochloride, N-n-heptyl-trans-4-aminomethylcyclohexanecarboxamide,N-n-hecptyl-trans-4-aminomethylcyclohexanecarboxamide hydrochloride, N-n-butyl-trans-4-aminomethylcyclohexanecarboxamide, N-n-butyl-trans-4-aminomethylcyclohyxanecarboxamide hydrochloride, N-n-propyl-trans-4-aminomethylcyclohexanecarboxamide, N-cyclohexyl-trans-4-aminomethylcyclohexanecarboxamide, N-cyclohexyl-trans-4-aminomethylcyclohexanecarboxamide hydrochloride, N,N-dicyclohexyl-trans-4-aminomethylcyclohexanecarboxamide, N,N-dicyclohexyl-trans-4-aminomethylcyclohexanecarboxamide hydrochloride, N,N-diethyl-trans-4-aminomethylcyclohexanecarboxamide, N,N-diethyl-trans-4-aminomethylcyclohexanecarboxamide hydrochloride, N-benzil-trans-4-aminomethylcyclohexanecarboxamide, N-benzil-trans-4-aminomethylcyclohexanecarboxamide hydrochloride, N-(4'-methoxyphenyl) trans-4-aminomethylcyclohexanecarboxamide, N-(4'-methoxyphenyl)-trans-4-aminomethylcyclohexanecarboxamide hydrochloride, N-(4'-ethoxy phenyl)-trans-4-aminomethylcyclohexanecarboxamide, N-(4'-ethoxy phenyl)-trans-4-aminomethylcyclohexanecarboxamide hydrochloride N-(2'-methyl phenyl)-trans-4-aminomethylcyclohexanecarboxamide, N-(2'-methyl phenyl)-trans-4-aminomethylcyclohexanecarboxamide hydrochloride, N-(3'-methyl phenyl)-trans-4-aminomethylcyclohexanecarboxamide N- (3'-methyl phenyl)-trans-4-aminomethylcyclohexanecarboxamide hydrochloride, N-(4'-chlorophenyl)-trans-4-aminomethylcyclohexanecarboxamide, N-(4'-chlorophenyl)-trans-4-aminomethylcyclohexanecarboxamide hydrochloride.

COMPOUND GROUP 2

General Formula (D)

It is possible to synthesize the amide derivatives and the salt of the tranexamic acid according to the present invention by the method described in, for example, J. Med. Chem., 15, 247(1972), JAPANESE PATENT LAID OPEN No. 48-68541. JAPANESE PATENT LAID OPEN No. 53-148536 or JAPANESE PATENT LAID OPEN No.57-59847.

The above-described compound can be in forms of inorganic salts such as sodium salt, potassium salt, ammonium salt, magnesium salt and calcium salt or organic salts such as monoethanolamine, diethanolamine and triethanolamine.

Preferable examples of the compounds are; Trans-4-acetylaminomethylcyclohexanecarboxylic acid, Trans-4-trifluoroacetylaminomethylcyclohexanecarboxylic acid, Trans-4-propionyllaminomethylcyclohexanecarboxylic acid, Trans-4-butyrylaminomethylcyclohexanecarboxylic acid, Trans-4-isobutyrylaminomethylcyclohexanecar- boxylic acid, Trans-4-valerylaminomethylcyclohexancar- boxylic acid, Trans-4-isovalerylaminomethylcyclohexane- carboxylic acid, Trans-4-pivaloylaminomethylcyclohexanecarboxylic acid, Trans-4-pentanoylaminomethylcyclohexanecarboxylic acid, Trans-4-hexanoylaminomethylcyclohexanecarboxylic acid, Trans-4-(2-hexenoylaminomethyl)cyclohexanecarboxylic acid, Trans-4-nonylaminomethylcyclohexanecarboxylic acid, Trans-4-(9-tetradecenoylaminomethyl)cyclohexanecarboxylic acid, Trans-4-decanoylaminomethylcyclohexanecarboxylic acid, Trans-4-palmitoylaminomethylcyclohexanecarboxylic acid, Trans-4-stearoylaminomethylcyclohexanecarboxylic acid, Trans-4-oleoylaminomethylcyclohexanecarboxylic acid, Trans-4-linoroylaminomethylcyclohexanecarboxylic acid, Trans-4-linolenoylaminomethylcyclohexanecarboxylic acid, Trans-4-(2,4,6-octatrienoylaminomethyl)cyclohexanecarboxylic acid, Trans-4-(trans-4'-n-pentylcyclohexylcarbonylaminomethyl)cyclohexane carboxylic acid, Trans-4-(trans-4'-isobutylcyclohexylcarbonylaminomethyl)cyclohexanecarboxylic acid, Trans-4-benzoylaminomethylcyclohexanecarboxylic acid, Trans-4-(3',4'-dimethoxycinnamoylaminomethyl)cyclohexanecarboxylic acid, Trans-4-(3',40',5'-trimethoxybenzoylaminomethyl)cyclohexanecarboxylic acid, Trans-4-(2'-aminobenzoylaminomethyl)cyclohexanecarboxylic acid, Trans-4-(2'-amino-5'-bromobenzoylaminomethyl)cyclohexanecarboxylic acid and, Trans-4-(3'-pyridylcarbonylaminomethyl)cyclohexanecarboxylic acid.

COMPOUND GROUP 3

General Formula (G)

It is possible to synthesize the derivatives and the salt of the tranexamic acid according to the present invention by the method described in, for example, JAPANESE PATENT LAID OPEN No.57-59847. Namely the compounds can be synthesized by, for example, (1) Acyl chloride method. (2) Mixed anhydride method, and (3) Activated ester method.

The above-described compounds can be in forms of an inorganic acid salt such as salt of hydrochloric acid, sulfuric acid phosphoric acid and hydrobromic acid or an organic acid salt such as salt of acetic acid, lactic acid, maleic acid, fumaric acid, tartaric acid, citric acid and methanesulfonic acid, and p-toluene sulfonic acid, an inorganic salts such as sodium salt, potassium salt, ammonium salt, magnesium salt, and calcium salt or organic salt such as monoethanolamine, diethanolamine and triethanolamine.

Preferably examples of the compounds are; L-glycyl-trans-4-aminomethylcyclohexanecarboxylic acid, L-seryl-trans-4-aminomethylcyclohexanecarboxylic acid, L-threonyl-trans-4-aminomethylcyclohexanecarboxylic acid, L-cysteinyl-trans-4-aminomethylcyclohexanecarboxylic acid, L-thyrosyl-trans-4-aminomethylcyclohexanecarboxylic acid, L-thyrosyl-trans-4-aminomethylcyclohexanecarboxylic acid, L-asparaginyl-trans-4-aminomethylcyclohexanecarboxylic acid, L-glutaminyl-trans-4-aminomethylcyclohexanecarboxylic acid, L-alanyl-trans-4-aminomethylcyclohexanecarboxylic acid, L-valyl-trans-4-aminomethylcyclohexanecarboxylic acid, L-leucyl-trans-4-aminomethylcyclohexanecarboxylic acid, L-isoleucyl-trans-4-aminomethylcyclohexanecarboxylic acid, L-prolyl-trans-4-aminomethylcyclohexanecarboxylic acid, L-phenylalanyl-trans-4-aminomethylcyclohexanecarboxylic acid, L-tryptophanyltrans-4-aminomethylcyclohexanecarboxylic acid, L-methionyl-trans-4-aminomethylcyclohexanecar- boxylic acid, L-α-aspartyl-trans-4-aminomethylcyclohex- anecarboxylic acid, L-α-glutamyl-trans-4-aminomethylcy- clohexanecarboxylic acid, L-lysyl-trans-4-aminomethylcy- clohexanecarboxylic acid, L-arginyl-trans-4-aminomethyl- cyclohexanecarboxylic acid, L-histidyl-trans-4-amino- methylcyclohexanecarboxylic acid and, L-ornithyl-trans-4-aminomethylcyclohexanecarboxylic acid.

COMPOUND GROUP 4

General Formula (H)

It is possible to synthesize the derivatives and the salt of the tranexamic acid according to the present invention by the method described in, for example, J. Med. Chem., 15,247 (1972).

The above-described compounds can be in forms of an inorganic acid salt such as salt of hydrochloric acid, sulfuric acid, hydrobromic acid, and phosphoric acid, or an organic acid salt such as salt of acetic acid, lactic acid, maleic acid, fumaric acid, tartaric acid, citric acid, methanesulfonic acid, and p-toluene sulfonic acid, or inorganic salts such as sodium salt, potassium salt, ammonium salt, magnesium salt, and calcium salt or organic salts such as monoethanolamine, diethanolamine and triethanolamine.

Preferable examples of the compounds are: Trans-4-methylaminomethylcyclohexanecarboxylic acid, Trans-4-methylaminomethylcyclohexanecarboxylic acid hydrochloride, Trans-4-ethylaminomethylcyclohexanecarboxylic acid, Trans-4-ethylaminomethylcyclohexanecarboxylic acid hydrochloride, Trans-4-dimethylaminomethytcyclohexancarboxylic acid, Trans-4-dimethylaminomethyl-cyclohexanecarboxylic acid hydrochloride, Trans-4-di-ethylaminomethylcyclohexanecarboxylic acid, Trans-4-di-ethylaminomethylcyclohexanecarboxylic acid hydrochloride, Trans-4-diisobutylaminomethylcyclohexanecarboxylic acid and, Trans-4-diisobutylaminomethylcyclohexanecarboxylic acid.

COMPOUND GROUP 5

(General Formula (I))

Examples of the R group of compound group 5 include the following:

a lower alkyl group such as methyl group, ethyl group, n-propyl group, isopropyl group, n-butyl group, isobutyl group, n-pentyl group, isopentyl group, n-hexyl group, isohexyl group, n-heptyl group, isoheptyl group or 2-ethyl hexyl group.

Examples of the $R_1$ group of compound group 5 include the following:

an alkyl group such as methyl group, ethyl group, n-propyl group, isopropyl group, n-butyl group, isobutyl group, n-pentyl group, isopentyl group, n-hexyl group, isohexyl group, n-heptyl group, isoheptyl group, 2-ethyl hexyl group;

a cycloalkyl group such as cyclopropyl group, cyclobutyl group, cyclopentyl group, cyclohexyl group, cycloheptyl group.

It is possible to synthesize the derivatives and the salt of tranexamic acid according to the present invention by method described in, for example, J. Med. Chem., 15,247 (1972) and JAPANESE PATENT LAID OPEN No.57-59852.

The above-described compounds can be in forms of inorganic salts such as sodium salt, potassium salt, ammonium salt, magnesium salt, and calcium salt or organic salts such as monoethanolamine, diethanolamine and triethanolamine.

Preferable examples of the compounds include the following: Trans-4-ureidomethylcyclohexanecarboxylic acid, Trans-4-(N'-ethylureidomethyl)cyclohexanecarboxylic acid, Trans-4-(N'-n-buty ureidomethyl)cyclohexanecarboxylic acid, Trans-4-(N'-ethoxycarbonylmethylureidmothyl) cyclohexanecarboxylic acid, Trans-4-(N'-cyclohexylureidomethyl)cyclohexanecarboxylic acid, Trans-4-(N'-phenylureidomethyl)cyclohexanecarboxylic acid, and Trans-4-(N'-2'-chlorophenylureidemethyl) cyclohexanecarboxylic acid.

COMPOUND GROUP 6

General Formula (J)

As an example of the R of the compound group 6:

a normal chain alkyl group such as methyl group, ethyl group, propyl group, butyl group, heptyl group and hexyl group, a branched chain alkyl group such as isopropyl group, isobutyl group, isopentyl group, octane-2-yl group, heptane-2-yl group, or a cyclic alkyl group such as cyclopentyl group, cyclohexyl group, and an arakyl group such as benzyl group, and pyridyl.

It is possible to synthesize the cyclohexanecarboxylic acid derivatives and the salt according to the present invention by the method described in, for example. JAPANESE PATENT LAID OPEN No.57-126461.

The above-described compounds can be in form of an inorganic acid salt such as salts of hydrochloric acid, sulfuric acid hydrofromic acid, phosphoric acid, and hydrobromic acid or an organic acid salt such as salts of acetic acid, lactic acid, maleic acid, fumaric acid, tartaric acid, citric acid, methanesulfonic acid, and p-toluene sulfonic acid, or inorganic salts such as sodium salt, potassium salt, ammonium salt, magnesium salt and calcium salt or organic salts such as monoethanolamine, diethanolamine and triethanolamine.

Preferable examples of the compounds include the following: Methyltrans-4-guanidinomethylcyclohexanecarboxylate, Ethyltrans-4-guanidinomethylcyclohexanecarboxylate, Propyltrans-4-guanidinomethylcyclohexanecarboxylate, Butyltrans-4-guanidinomethylcyclohexanecarboxylate, Heptyltrans-4-guanidinomethylcyclohexanecarboxylate Isopropyltrans-4-guanidinomethylcyclohexanecarboxylate, Isobutyltrans-4-guanidinomethylcyclohexanecarboxylate, Octane-2-yl-trans-4-guanidinomethylcyclohexanecarboxylate, Heptane-2-yl-trans-4-guanidinomethylcyclohexanecarboxylate, Cyclopentyltrans-4-guanidinomethylcyclohexanecaroboxylate, Cyclohexyltrans-4-guanidinomethylcyclohexanecarboxylate, Benzyltrans-4-guanidinomethylcyclohexanecarboxylate, and 4'-pyridylmethyltrans-4-guanidinomethylcyclohexanecarboxylate.

COMPOUND GROUP 7

General Formula (K)

As examples of the R of the compound group 7, methyl group, ethyl group, propyl group, butyl group, isopropyl group, isobutyl group, and t-butyl group are cited.

It is possible to synthesize the trans-4-guanidinomethyl cyclohexanecarboxylic acid derivatives and the salt according to the present invention by the method described in, for example, JAPANESE PATENT LAID OPEN No.57-21360. JAPANESE PATENT LAID OPEN No.57-48960.

The above-described compounds can be in the form of an inorganic acid salt such as salts of hydrochloric acid, sulfuric acid, phosphoric acid, and hydrobromic acid or an organic acid salt such as salts of acetic acid, lactic acid, maleic acid, fumaric acid, tartaric acid, citric acid, methanesulfonic acid and p-toluene sulfonic acid.

Preferable examples of the compounds include the following: Trans-4-guanidinomethylcyclohexanecarboxylic acid 2'-phenoxycarbonyl phenyl ester, Trans-4-guanidinomethylcyclohexanecarboxylic acid 4'-phenoxycarbonyl phenyl ester, Trans-4-guanidinomethylcyclohexanecarboxylic acid 3'-benzyloxycarbonyl phenyl ester, Trans-4-guanidinomethylcyclohexanecarboxylic acid 4'-benzyloxycarbonyl phenyl ester, Trans-4-guanidinomethylcyclohexanecarboxylic acid 3'-carboxyphenylester, Trans-4-guanidinomethylcyclohexanecarboxylic acid 4'-ethoxy carbonyl phenyl ester, Trans-4-guanidinomethylcyclohexanecarboxylic acid 4'-carboxyphenyl ester, Trans-4-guanidinomethylcyclohexanecarboxylic acid 3'-methoxycarbonylphenyl ester, Trans-4-guanidinomethylcyclohexanecarboxylic acid 4'-carboxymethylphenyl ester, Trans-4-guanidinomethylcyclohexanecarboxylic acid 4'-t-butyloxycarbonylmethylphenyl ester, Trans-4-guanidinomethylcyclohexanecarboxylic acid 4'-(2-carboxyethyl)phenyl ester, Trans-4-guanidinomethylcyclohexanecarboxylic acid 4'-(2-ethoxycarbonyl ethyl)phenyl ester.

COMPOUND GROUP 8

General Formula (L)

Examples of the $R_1$, $R_2$ and $R_3$ of the compound group 8 include:

lower alkyl group such as methyl group, ethyl group, propyl group, butyl group, isopropyl group, isobutyl group, t-butyl group;

lower alkoxy group such as methoxy group, ethoxy group, propoxy group and butoxy group;

alkanoyl group such as acetyl group, propyonil group, butyryl group; and a halogen atom such as chlorine atom, bromine atom, iodia atom, fluorine atom.

It is possible to synthesize the trans-4-guandinomethyl-cyclohexanecarboxylic acid derivatives and the salt according to the present invention by the method described in, for example, JAPANESE PATENT LAID OPEN No. 57-16856, JAPANESE PATENT LAID OPEN No. 57-122059, JAPANESE PATENT LAID OPEN No. 57-122061, and JAPANESE PATENT LAID OPEN No. 57-122062.

The above-described compounds can be in forms of an inorganic acid salt such as salt of hydrochloric acid, sulfuric acid, hydrobromic acid, phosphoric acid, and hydrobromic acid, or an organic acid salt such as salt of acetic acid, lactic acid, maleic acid, fumaric acid, tartaric acid, citric acid, methanesulfonic acid, and p-toluene sulfonic acid.

Preferable examples of the compounds include: Trans-4-guanidinomethylcyclohexanecarboxylic acid phenyl ester, Trans-4-guanidinomethylcyclohexanecarboxylic acid 4'-methylphenyl ester, Trans-4-guanidinomethylcyclohexanecarboxylic acid 4'-ethylphenyl ester, Trans-4-guanidinomethylcyclohexanecarboxylic acid 2'-methoxyphenyl ester, Trans-4-guanidinomethylcyclohexanecarboxylic acid 4'-methoxyphenyl ester, Trans-4-guanidinomethylcyclohexanecarboxylic acid 2'-ethoxyphenyl ester, Trans-4-guanidinomethylcyclohexanecarboxylic acid 2'-acetylphenyl ester, Trans-4-guanidinomethylcyclohexanecarboxylic acid 4'-acetylphenyl ester, Trans-4-guanidinomethylcyclohexanecarboxylic acid 2'-phenylphenyl ester, Trans-4-guanidinomethylcyclohexanecarboxylic acid 4'-phenylphenyl ester, Trans-4-guanidinomethylcyclohexanecarboxylic acid 2'-chlorophenyl ester, Trans-4-guanidinomethylcyclohexanecarboxylic acid 4'-chlorophenyl ester, Trans-4-guanidinomethylcyclohexanecarboxylic acid 4'-bromophenyl ester, Trans-4-guanidinomethylcyclohexanecarboxylic acid 4'-iodinephenyl ester, Trans-4-guanidinomethylcyclohexanecarboxylic acid 3',4'-dichlorophenyl ester, Trans-4-guanidinomethylcyclohexanecarboxylic acid 2',4',6'-trichlorophenyl ester, Trans-4-guanidinomethylcyclohexanecarboxylic acid 3'-trifluoromethylphenyl ester, Trans-4-guanidinomethylcyclohexanecarboxylic acid 4'-nitrophenyl ester, Trans-4-guanidinomethylcyclohexanecarboxylic acid 4'-acetoaminophenyl ester, Trans-4-guanidinomethylcyclohexanecarboxylic acid 4'-sulfamoylphenyl ester, Trans-4-guanidinomethylcyclohexanecarboxylic acid 4'-benzoylphenyl ester, Trans-4-guanidinomethylcyclohexanecarboxylic acid 2'-phenoxylphenyl ester, Trans-4-guanidinomethylcyclohexanecarboxylic acid 2'-benzyloxyphenyl ester, Trans-4-guanidinomethylcyclohexanecarboxylic acid 2'-formylphenyl ester, Trans-4-guanidinomethylcyclohexanecarboxylic acid 4'-formylphenyl ester, Trans-4-guanidinomethylcyclohexanecarboxylic acid 2'-cyanophenyl ester, Trans-4-guanidinomethylcyclohexanecarboxylic acid 4'-cyanophenyl ester, and Trans-4-guanidinomethylcyclohexanecarboxylic acid 2'-isopropyl-4'-chloro-5'-methylphenyl ester.

COMPOUND GROUP 9

General Formula (M)

An example of the A of the compound group 9 includes a pyridyl group such as 2-pyridyl group, 3-pyridyl group, 4-pyridyl group.

An example of the $X_3$ includes a halogen atom such as chlorine atom, bromine atom, iodine atom and a fluorine atom are cited.

It is possible to synthesize the cyclohexanececarboxylic acid derivatives and the salt according to the present invention by the method described in, for example, JAPANESE PATENT PUBLISH No. 63-12055, JAPANESE PATENT PUBLISH No. 63-46736. JAPANESE PATENT LAID OPEN No. 57-116035, and JAPANESE PATENT LAID OPEN No. 57-140714.

Preferable examples of the compounds are Trans-4-benzylideneaminomethylcyclohexanecarboxylic acid, Trans-4-(2'-nitrobenzylideneaminomethyl)cyclohexanecarboxylic acid, Trans-4-(3'-nitrobenzylideneaminomethyl)cyclohexanecarboxylic acid, Trans-4-(4'-nitrobenzylideneaminomethyl)cyclohexanecarboxylic acid, Trans-4-(2'-hydroxybenzylideneaminomethyl)cyclohexanecarboxylic acid, Trans-4-(3'-hydroxybenzylideneaminomethyl)cyclohexanecarboxylic acid, Trans-4-(4'-hydroxybenzylideneaminomethyl)cyclohexanecarboxylic acid, Trans-4-(2'-methoxybenzylideneaminomethyl)cyclohexanecarboxylic acid, Trans-4-(3'-methoxybenzylideneaminomethyl) cyclohexanecarboxylic acid, Trans-4-(4'-methoxybenzylideneaminomethyl)cyclohexanecarboxylic acid, Trans-4-(3'-carboxy-4'-hydroxy-benzylideneaminomethyl)cyclohexanecarboxylic acid, Trans-4-(3',4',5'-trimethoxybenzylideneaminomethyl) cyclohexanecarboxylic acid, Trans-4-(3',4',5'-trihydroxybenzylidenaminomethyl)cyclohexanecarboxylic acid, Trans-4-(3',4'-dimethoxybenzylideneaminomethyl) cyclohexanecarboxylic acid, Trans-4-(2',3'-dimethoxybenzylideneaminomethyl)cyclohexanecarboxylic acid, Trans-4-(2',4'-dimethoxybenzylideneaminomethyl) cyclohexanecarboxylic acid, Trans-4-(2',5'-dimethoxybenzylideneaminomethyl)cyclohexanecarboxylic acid, Trans-4-(3',5'-dimethoxybenzylideneaminomethyl) cyclohexanecarboxylic acid, Trans-4-(3',4'-dihydroxybenzylideneaminomethyl)cyclohexanecarboxylic acid, Trans-4-(2',3'-dihydroxybenzylideneaminomethyl) cyclohexanecarboxylic acid, Trans-4-(2',4'-dihydroxybenzylideneaminomethyl)cyclohexanecarboxylic acid, Trans-4-(2',5'-dihydroxybenzylideneaminomethyl) cyclohexanecarboxylic acid, Trans-4-(3',5'-dihydroxybenzylideneaminomethyl) cycloyyhexanecarboxylic acid, Trans-4-(4'-chlorobenzylideneaminomethyl)cyclohexanecarboxylic acid, Trans-4-(2'-chlorobenzylideneaminomethyl) cyclohexanecarboxylic acid, Trans-4-(3'-trifluoromethylbenzylideneaminomethyl)cyclohexane carboxylic acid, Trans-4-(3'-pyridylmethylideneaminomethyl) cyclohexanecarboxylic acid, Trans-4-(4'-pyridylmethylideneaminomethyl)cyclohexanecarboxylic acid, Trans-4-(4'-isopropenylbenzylideneaminomethyl) cyclohexanecarboxylic acid, and Trans-4-(3',4'-dihydroxybenzylideneaminomethyl)cyclohexanecarboxylic acid ethyl ester.

The external preparation for the skin according to the present invention contains one or more than two types of the derivatives of tranexamic acid. The content of the derivatives is from 0.001 to 20 weight % in the total amount of external preparation, and more preferably from 0.01 to 7 weight %. If the content is less than 0.001 weight %, it is difficult to obtain the depigmentation effect and the skin care effect. Also, even if the content is more than 20 weight %, the further improvement might not be obtained.

It is possible to add other ingredients which can be generally used for an external preparation for the skin such as cosmetics and medical supplies to the external preparation for the skin according to the present invention. For example, it is possible to add oil, an ultraviolet ray absorbent, an antioxidant. a surface-active agent, a moisture agent, a perfume, water, alcohol, a thickener, a color agent, and a skin nutrition agent (tocopherol acetate, pantothenyl ethyl ether, salt of glycyrrhizic acid).

EXAMPLES

The composition of the present invention is explained in detail by the following examples. It should be noted that the present invention is not limited by these examples. The content is expressed by weight %.

The examination methods carried out in these examples are explained before the description of the examples.

COMPOUND GROUP 1

(1) Depigmentation Effect

Preparation of Sample

Lotions were prepared by the following formula, using each sample. Namely, the alcohol phase and aqueous phase according to the following foumula were prepared respectively, and both phases were mixed and dissolved according to an ordinal method.

| | Weight % |
|---|---|
| Alcohol phase | |
| 95% ethyl alcohol | 25.0 |
| Polyoxyethylene (25 moles) hydrogenated castor oil ether | 2.0 |
| Antioxidant and antiseptic | q.s. |
| Perfume | q.s. |
| Composition (TABLE 1) | 1.0 |
| Aqueous phase: | |
| Glyercol | 5.0 |
| Sodium hexametaphosphate | q.s. |
| Ion exchanged water | balance |

Examination Method 10 subjects for each group were disposed under sunlight in the summer for 4 hours (2 hours×2 days). The lotion was applied to the skin of the medial brachia once each morning and once in the evening for 5 days after the day exposed to the sun light for 8 weeks. After the application period, the depression of the pigmentation effect, which was caused by the sun light irradiation, was examined and evaluated the degree based on the following standard.

Standard

⊙: The number of the subjects who judged the result was "extremely effective" or "effective" were equal to or more than 80%

○: The number of the subjects who judged the result was "extremely effective" or "effective" were from 50% to 80%
Δ: The number of the subjects who judged the result was "extremely effective" or "effective" were from 30 to 50% ×: The number of the subjects who judged the result was "extremely effective" or "effective" were less than 30%.

The results are shown in TABLE 1.

TABLE 1

| | COMPOUND | DEPIGMENTATION EFFECT |
|---|---|---|
| COMPARISON 1 | NONE | × |
| COMPARISON 2 | HYDROQUINONE | Δ |
| EXAMPLE 1 | N-n-hexyl-trans-4-aminomethyl cyclohexane-carboxamide hydrochloride | ⊙ |
| EXAMPLE 2 | Trans-4-aminomethylcyclohexane carboxamide | ⊙ |
| EXAMPLE 3 | N-(p-methoxy)phenyl-trans-4-aminomethylcyclohexane-carboxamide | ⊙ |

As is clear from the TABLE 1, the external preparation for the skin according to Examples 1 to 3 could suppress deposition of melanic pigment and, therefore, prevent suntan.

(2) Skin Care Effect

The external preparation for skin according to the Examples 1 to 3 were applied to the left half of the faces of the subjects, and the preparation according to comparison 1 was applied to the right half of the faces of the subjects after washing the faces every morning and night for two weeks.

One group of subjects included 10 women and 3 group of subjects were examined.

The results of the examination were evaluated and the degree based on the following standard for moisturising effect, texture of skin surface, and maintenance of moisturising effect.

Standard

⊚: The number of the subjects who judged the result was "extremely effective" or "effective" were equal to or more than 80%

○: The number of the subjects who judged the result was "extremely effective" or "effective" were from 50% to 80%
Δ: The number of the subjects who judged the result was "extremely effective" or "effective" were from 30% to 50%
×: The number of the subjects who judged the result was "extremely effective" or "effective" were less than 30%.

The results are shown in TABLE 2.

TABLE 2

|  | moisturising effect | texture of skin surface | maintenance of moisturising effect |
| --- | --- | --- | --- |
| COMPARISON 1 | x | x | x |
| EXAMPLE 1 | ⊚ | ⊚ | ⊚ |
| EXAMPLE 2 | ⊚ | ⊚ | ⊚ |
| EXAMPLE 3 | ⊚ | ⊚ | ⊚ |

As is clear from TABLE 2, the external preparation for the skin according to Examples 1 to 3 had excellent skin care effect.

| EXAMPLE 4 CREAM | weight % |
| --- | --- |
| Stearic acid | 5.0 |
| Stearyl alcohol | 4.0 |
| Isopropyl myristate | 18.0 |
| Glycerine monostearate | 3.0 |
| Propylene glycol | 10.0 |
| Trans-4-aminomethylcyclohexanecarboxamide | 20.0 |
| Caustic potash | 0.2 |
| Sodium hydrogensulfite | 0.01 |
| Antiseptic | q.s. |
| Perfume | q.s. |
| Ion exchanged water | balance |

Manufacturing Method

The propylene glycol and caustic potash were added to the ion exchanged water, dissolved and heated to 70° C. (Aqueous phase). The other ingredients were mixed, heated, melted and kept at 70° C. (Oil phase). The oil phase was added to the aqueous phase gradually. After addition of the oil phase, the temperature was kept constant and the reaction completed. The system was uniformly emulsified with the homomixer and cooled to 30° C. under stirring conditions.

| EXAMPLE 5 CREAM | weight % |
| --- | --- |
| Stearic acid | 6.0 |
| Sorbitane monostearate | 2.0 |
| Polyoxyethylene (20 moles) sorbitanemonostearate | 1.5 |
| Propylene glycol | 10.0 |
| N-n-hexyl-trans-4-aminomethylcyclohexanecarboxamide hydrochloride | 7.0 |
| Glycerine trioctanoate | 10.0 |

-continued

| EXAMPLE 5 CREAM | weight % |
| --- | --- |
| Squalene | 5.0 |
| Sodium hydrogensulfite | 0.01 |
| Ethylparaben | 0.3 |
| Perfume | q.s. |
| Ion exchanged water | balance |

Manufacturing Method

The propylene glycol was added to the ion exchanged water, dissolved and heated to 70° C. (Aqueous phase). The other ingredients were mixed, heated, melted and kept at 70° C. (Oil phase). The oil phase was added to the aqueous phase and preemulsified. The system was uniformly emulsified with the homomixer and cooled to 30° C. under stirring conditions.

| EXAMPLE 6 CREAM | weight % |
| --- | --- |
| Stearyl alcohol | 7.0 |
| Stearic acid | 2.0 |
| Hydrogenated lanoline | 2.0 |
| Squalane | 5.0 |
| 2-octyldodesylalcohol | 6.0 |
| Polyoxyethylene (25 moles) cetylalcohol ether | 3.0 |
| Glycerinemonostearate | 2.0 |
| Propylene glycol | 5.0 |
| N-n-propyl-trans-4-aminomethylcyclohexanecarboxamide | 0.005 |
| Perfume | q.s. |
| Sodiumm hydrogensulfite | 0.03 |
| Ethylparaben | 0.3 |
| Ion exchanged water | balance |

Manufacturing Method

The propylene glycol was added to the ion exchanged water, dissolved and heated to 70° C. (Aqueous phase). The other ingredients were mixed, heated, melted and kept at 70° C. (Oil phase). The oil phase was added to the aqueous phase and preemulsified. The system was uniformly emulsified with the homomixer and cooled to 30° C. under stirring conditions.

| EXAMPLE 7 MILKY LOTION | weight % |
| --- | --- |
| Stearic acid | 2.5 |
| Cetyl alcohol | 1.5 |
| Petrolatum | 5.0 |
| Liquid paraffin | 10.0 |
| Polyoxyethylene (10 moles) monoleate | 2.0 |
| Polyethylene glycol 1500 | 3.0 |
| Triethanolamine | 1.0 |
| N-benzil-trans-4-aminomethylcyclohexanecarboxamide | 10.0 |
| Sodium hydrogensulfite | 0.01 |
| Ethylparaben | 0.3 |
| Carboxyvinyl polymer | 0.05 |
| Perfume | q.s. |
| Ion exchanged water | balance |

Manufacturing Method

The carboxyvinyl polymer was dissolved in a part of the ion exchanged water (A phase). The polyethylene glycol 1500 and the triethanolamine were added to the other part of the ion exchanged water, dissolved, heated and kept at 70° C. (aqueous phase). The other agents were mixed, heated, melted and kept at 70° C. (Oil phase). The oil phase was added to the aqueous phase and preemulsified. The system was uniformly emulsified with the homomixer and cooled to 30° C. under stirring conditions.

| EXAMPLE 8 MILKY LOTION | weight % |
|---|---|
| Oil phase: | |
| Stearyl alcohol | 1.5 |
| Squalene | 2.0 |
| Petrolatum | 2.5 |
| Deodorized liquid lanoline | 1.5 |
| Evening primrose oil | 2.0 |
| Isopropyl myristate | 5.0 |
| Glycerine monooleate | 2.0 |
| Polyoxyethylene (60 moles) hydrogenated castor oil | 2.0 |
| Tocopherol acetate | 0.05 |
| Ethylparaben | 0.2 |
| Butylparaben | 0.1 |
| N-(p-methoxy)phenyl-1-trans-4-aminomethyl-cyclohexanecarboxamide | 1.0 |
| Trans-4-aminomethylcyclohexanecarboxamide hydrochloride | 1.0 |
| Perfume | q.s. |
| Aqueous phase: | |
| Sodium hydrogensulfite | 0.01 |
| Glycerol | 5.0 |
| Sodium hyaluronate | 0.01 |
| Carboxyvinyl polymer | 0.2 |
| Potassium hydroxide | 0.2 |
| Purified water | balance |

Manufacturing Method

The oil phase agents were dissolved at 70° C. The aqueous phase agents were dissolved at 70° C. The oil phase was added to the aqueous phase and the system was uniformly emulsified with the homomixer and cooled to 30° C. with a heat exchanger.

| EXAMPLE 9 JELLY | weight % |
|---|---|
| 95% ethyl alcohol | 10.0 |
| Dipropyleneglycol | 15.0 |
| Polyoxyethylene (50 moles) oleylalcohol ether | 2.0 |
| Carboxyvinyl polymer | 1.0 |
| Caustic soda | 0.15 |
| L-arginine | 0.1 |
| N,N-diethyl-trans-4-aminomethylcyclohexanecarboxamide hydrochloride | 1.0 |
| N-1-napthyl-trans-4-aminomethylcyclohexanecarboxamide | 1.0 |
| 4-hydroxybenzoic acid methylester | 0.2 |
| Perfume | q.s. |
| Ion exchanged water | balance |

Manufacturing Method

The carboxyvinyl polymer was uniformly dissolved in the ion exchanged water. The N,N-diethyl-trans-4-aminomethylcyclohexanecarboxamide hydrochloride, N-1-naphthyl-trans-4-aminomethylcyclohexanecarboxamide, polyoxyethylene (50 moles) oleyl alcohol ether were dissolved in the 95% ethanol. The ethanol phase was added to the aqueous phase and the other ingredients were added. The system was neutralized and thicked by the caustic soda and L-arginine.

| EXAMPLE 10 LOTION | weight % |
|---|---|
| A phase: | |
| Ethanol (95%) | 10.0 |
| Poloxyethylene (20 moles) octyldodecanol | 1.0 |
| 4-hydroxybenzoic acid methylester | 0.15 |
| Pantothenyl ethylether | 0.1 |
| Trans-4-aminomethylcyclohexanecarboxamide hydrochloride | 0.05 |
| B phase: | 0.1 |
| Potassium hydroxide | |
| C phase: | |
| Glycerol | 5.0 |
| Dipropyleneglycol | 10.0 |
| Sodium hydrogensulfite | 0.03 |
| Carboxyvinyl polymer | 0.2 |
| Purified water | balance |

Manufacturing Method

The A phase, B phase and C phase were uniformly dissolved, respectively. The A phase was dissolved in the C phase, the B phase was added and the system was packed.

| EXAMPLE 11 PACK | weight % |
|---|---|
| A phase: | |
| Dipropyleneglycol | 5.0 |
| Polyoxyethylene (60 moles) hydrogenated castor oil | 5.0 |
| B phase: | |
| N-n-butyl-trans-4-aminomethylcyclohexanecarboxamide hydrochloride | 1.0 |
| Trans-4-aminomethylcyclohexanecarboxamide hydrochloride | 1.0 |
| Olive oil | 5.0 |
| Tocopherol acetate | 0.2 |
| Ethylparaben | 0.2 |
| Perfume | 0.2 |
| C phase: | |
| Sodium hydrogensulfite | 0.03 |
| Polyvinyl alcohol (saponification degree 90, degree of polymerization 2000) | 13.0 |
| Ethanol | 7.0 |
| Purified water | balance |

Manufacturing Method

The A phase, B phase and C phase were uniformly dissolved, respectively. The B phase was dissolved in the A phase, and the C phase was added and the system was packed.

The external preparation for the skin according to Examples 4 to 11 had excellent depigmentation effect as well as skin care effects.

COMPOUND GROUP 2

(1) Depigmentation Effect

The depigmentation effect of the compound group 2 was examined according to the method described above.

The results are shown in TABLE 3.

TABLE 3

| | COMPOUND | DEPIGMENTATION EFFECT |
|---|---|---|
| COMPARISON 1 | NONE | x |
| COMPARISON 2 | HYDROQUINONE | Δ |
| EXAMPLE 12 | Trans-4-(trans-4'-isobutyl-cyclohexylcarbonylamino-methyl) cyclohexane carboxylic acid | ⊚ |
| EXAMPLE 13 | Sodium trans-4-oleoylamino-methylcyclohexane carboxylic acid | ⊚ |
| EXAMPLE 14 | Trans-4-(3',4'-dimethoxy-cinnamoylaminomethyl) cyclohexanecarboxylic acid | ⊚ |

As is clear from TABLE 3. the external preparation for the skin according to Examples 12 to 14 could also suppress deposition of melanoic pigment and suntan.

(2) Skin Care Effect

The skin care effect of the compound group 2 was examined according to the method described above.
The results are shown in TABLE 4.

TABLE 4

| | moisturising effect | texture of skin surface | maintenance of moisturising effect |
|---|---|---|---|
| COMPARISON 1 | x | x | x |
| EXAMPLE 12 | ⊚ | ⊚ | ⊚ |
| EXAMPLE 13 | ⊚ | ⊚ | ⊚ |
| EXAMPLE 14 | ⊚ | ⊚ | ⊚ |

As is clear from TABLE 4, the external preparation for skin according to Examples 12 to 14 had excellent skin care effect.

| EXAMPLE 15 CREAM | weight % |
|---|---|
| Stearic acid | 5.0 |
| Stearyl alcohol | 4.0 |
| Isopropyl myristate | 18.0 |
| Glycerine mono stearate | 3.0 |
| Propylene glycol | 10.0 |
| Trans-4-acetylaminomethylcyclohexanecarboxylic acid | 20.0 |
| Caustic potash | 0.2 |
| Sodium hydrogensulfite | 0.01 |
| Antiseptic | q.s. |
| Perfume | q.s. |
| Ion exchanged water | balance |

Manufacturing Method

The preparation with respect to the present example was prepared by the same method described in the explanation of example 4.

| EXAMPLE 16 CREAM | weight % |
|---|---|
| Stearic acid | 6.0 |
| Sorbitane monostearate | 2.0 |
| Polyoxyethylene (20 moles) sorbitanmonostearate | 1.5 |
| Propylene glycol | 10.0 |
| Trans-4-palmitoylaminomethylcyclohexanecarboxylic acid | 7.0 |
| Glycerine trioctanoate | 10.0 |
| Squalene | 5.0 |
| Sodium hydrogensulfite | 0.01 |
| Ethylparaben | 0.3 |
| Perfume | q.s. |
| Ion exchanged water | balance |

Manufacturing Method

The preparation with respect to the present example was prepared by the same method described in the explanation of example 5.

| EXAMPLE 17 CREAM | weight % |
|---|---|
| Stearyl alcohol | 7.0 |
| Stearic acid | 2.0 |
| Hydrogenated lanoline | 2.0 |
| Squalane | 5.0 |
| 2-octyldodecylalcohol | 6.0 |
| Polyoxyethylene (25 moles) cetylalcohol ether | 3.0 |
| Glycerinemonostearate | 2.0 |
| Propylene glycol | 5.0 |
| Trans-4-(2'-aminobenzoylaminomethyl) cyclohexanecarboxylic acid | 0.005 |
| Perfume | q.s. |
| Sodium hydrogensulfite | 0.03 |
| Ethylparaben | 0.3 |
| Ion exchanged water | balance |

Manufacturing Method

The preparation with respect to the present example was prepared by the same method described in the explanation of example 6.

| EXAMPLE 18 MILKY LOTION | weight % |
|---|---|
| Stearic acid | 2.5 |
| Cetyl alcohol | 1.5 |
| Petrolatum | 5.0 |
| Liquid paraffin | 10.0 |
| Polyoxyethylene (10 moles) monoleate | 2.0 |
| Polyethylene glycol 1500 | 3.0 |
| Triethanolamine | 1.0 |
| Trans-4-bezoylaminomethylcyclohexanecarboxylic acid | 10.0 |
| Sodium hydrogensulfite | 0.01 |
| Ethylparaben | 0.3 |
| Carboxyvinyl polymer | 0.05 |
| Perfume | q.s. |
| Ion exchanged water | balance |

Manufacturing Method

The preparation with respect to the present example was prepared by the same method described in the explanation of example 7.

| EXAMPLE 19 MILKY LOTION | weight % |
|---|---|
| Oil phase | |
| Stearyl alcohol | 1.5 |
| Squalene | 2.0 |
| Petrolatum | 2.5 |

| EXAMPLE 19 MILKY LOTION | weight % |
|---|---|
| Deodorized liquid lanoline | 1.5 |
| Evening primrose oil | 2.0 |
| Isopropyl myristate | 5.0 |
| Glycerine monooleate | 2.0 |
| Polyoxyethylene (60 moles) hydrogenated castor oil | 2.0 |
| Tocopherol acetate | 0.05 |
| Ethylparaben | 0.2 |
| Butylparaben | 0.1 |
| Trans-4-decanoylaminomethycyclohexanecarboxylic acid cyclohexanecarboxylic acid | 1.0 |
| Trans-4-decanoylaminomethylcyclohexanecarboxylic acid | 1.0 |
| Perfume | q.s. |
| Aqueous phase | |
| Sodium hydrogensulfite | 0.01 |
| Glycerol | 5.0 |
| Sodium hyaluronate | 0.01 |
| Carboxyvinyl polymer | 0.2 |
| Potassium hydroxide | 0.2 |
| Purified water | balance |

Manufacturing Method

The preparation with respect to the present example was prepared by the same method described in the explanation of example 8.

| EXAMPLE 20 JELLY | weight % |
|---|---|
| 95% ethyl alcohol | 10.0 |
| Dipropyleneglycol | 15.0 |
| Polyxoyethylene (50 moles) oleylalcohol ether | 2.0 |
| Carboxyvinyl polymer | 1.0 |
| Caustic soda | 0.15 |
| L-arginine | 0.1 |
| Trans-4-trifluoroacetylcyclohexanecarboxylic acid | 1.0 |
| Sodium trans-4-linoleylaminomethylcyclohexanecarboxylic acid | 1.0 |
| 4-hydroxybenzoic acid methylester | 0.2 |
| Perfume | q.s. |
| Ion exchanged water | balance |

Manufacturing Method

The preparation with respect to the present example was prepared by the same method described in the explanation of example 9.

| EXAMPLE 21 LOTION | weight % |
|---|---|
| A phase: | |
| Ethanol (95%) | 10.0 |
| Polyoxyethylene (20 moles) octyldodecanol | 1.0 |
| 4-hydroxybenzoic acid methylester | 0.15 |
| Pantothenyl ethylether | 0.1 |
| Trans-4-(3'-pyridylcarbonylaminomethyl)cyclohexane carboxylic acid | 0.05 |
| B phase: | 0.1 |
| Potassium hydroxide | |
| C phase: | |
| Glycerol | 5.0 |
| dipropyleneglycol | 10.0 |
| Sodium hydrogensulfite | 0.03 |
| Carboxyvinyl polymer | 0.2 |
| Purified water | balance |

Manufacturing Method

The preparation with respect to the present example was prepared by the same method described in the explanation of example 10.

| EXAMPLE 22 PACK | weight % |
|---|---|
| A phase: | |
| Dipropyleneglycol | 5.0 |
| Polyoxyethylene (60 moles) hydrogenated castor oil | 5.0 |
| B phase: | |
| Sodium trans-4-(2',4',6'-octatrienoylaminomethyl)cyclohexane carboxylic acid | 1.0 |
| Trans-4-trifluoroacetylaminomethylcyclohexane carboxylic acid | 1.0 |
| Olive oil | 5.0 |
| Tocopherol acetate | 0.2 |
| Ethylparaben | 0.2 |
| Perfume | 0.2 |
| C phase: | |
| Sodium hydrogensulfite | 0.03 |
| Polyvinyl alcohol (saponification degree 90, degree of polymerization 2000) | 13.0 |
| Ethanol | 7.0 |
| Purified water | balance |

Manufacturing Method

The preparation with respect to the present example was prepared by the same method described in the explanation of example 11.

COMPOUND GROUP 3

(1) Depigmentation Effect

The depigmentation effect of the compound group 3 was examined according to the method described above.

The results are shown in TABLE 5.

TABLE 5

| | COMPOUND | DEPIGMENTATION EFFECT |
|---|---|---|
| COMPARISON 1 | NONE | x |
| COMPARISON 2 | HYDROQUINONE | Δ |
| EXAMPLE 23 | L-alanyl-trans-4-aminomethyl cyclohexanecarboxylic acid | ⊙ |
| EXAMPLE 24 | L-varyl-aminomethylcyclo-hexane carboxylic acid | ⊙ |
| EXAMPLE 25 | L-threonyl-trans-4-amino-methyl cyclohexane-carboxylic acid | ⊙ |

As is clear from TABLE 5, the external preparation for the skin according to Examples 23 to 25 could also suppress deposition of melanoic pigment and suntan.

(2) Skin Care Effect

The skin care effect of the compound group 3 was examined according to the method described above.

The results are shown in TABLE 6.

TABLE 6

| | moisturising effect | texture of skin surface | maintenance of moisturising effect |
|---|---|---|---|
| COMPARISON 1 | x | x | x |
| EXAMPLE 23 | ⊙ | ⊙ | ⊙ |
| EXAMPLE 24 | ⊙ | ⊙ | ⊙ |
| EXAMPLE 25 | ⊙ | ⊙ | ⊙ |

As is clear from TABLE 6, the external preparation for the skin according to Examples 23 to 25 had excellent skin care effect.

| EXAMPLE 26 CREAM | weight % |
|---|---|
| Stearic acid | 5.0 |
| Stearyl alcohol | 4.0 |
| Isopropyl myristate | 18.0 |
| Glycerine monostearate | 3.0 |
| Propylene glycol | 10.0 |
| L-leucyl-trans-4-aminomethylcyclohexanecarboxylic acid | 20.0 |
| Caustic potash | 0.2 |
| Sodium hydrogensulfite | 0.01 |
| Antiseptic | q.s. |
| Perfume | q.s. |
| Ion echanged water | balance |

Manufacturing Method

The preparation with respect to the present example was prepared by the same method described in the explanation of example 4.

| EXAMPLE 27 CREAM | weight % |
|---|---|
| Stearic acid | 6.0 |
| Sorbitane monostearate | 2.0 |
| Polyoxyethylene (20 moles) sorbitanemonostearate | 1.5 |
| Propylene glycol | 10.0 |
| L-alanyl-trans-4-aminomethylcyclohexanecarboxylic acid | 7.0 |
| Glycerine trioctanoate | 10.0 |
| Squalene | 5.0 |
| Sodium hydrogensulfite | 0.01 |
| Ethylparaben | 0.3 |
| Perfume | q.s. |
| Ion exchanged water | balance |

Manufacturing Method

The preparation with respect to the present example was prepared the same method described in the explanation of example 5.

| EXAMPLE 28 CREAM | weight % |
|---|---|
| Stearyl alcohol | 7.0 |
| Stearic acid | 2.0 |
| Hydrogenated lanoline | 2.0 |
| Squalane | 5.0 |
| 2-octyldodesylalcohol | 6.0 |
| Polyoxyethylene (25 moles) cetylalcohol ether | 3.0 |
| Glycerinemonostearate | 2.0 |
| Propylene glycol | 5.0 |
| L-valyl-trans-4-aminomethylcyclohexanecarboxylic acid | 0.005 |
| Perfume | q.s. |
| Sodium hydrogensulfite | 0.03 |
| Ethylparaben | 0.3 |
| Ion exchanged water | balance |

Manufacturing Method

The preparation with respect to the present example was prepared by the same method described in the explanation of example 6.

| EXAMPLE 29 MILKY LOTION | weight % |
|---|---|
| Stearic acid | 2.5 |
| Cetyl alcohol | 1.5 |
| Petrolatum | 5.0 |
| Liquid paraffin | 10.0 |
| Polyoxyethylene (10 moles) monoleate | 2.0 |
| Polyethylene glycol 1500 | 3.0 |
| Triethanolamine | 1.0 |
| L-glycyl-trans-4-aminomethylcyclohexanecarboxylic acid | 10.0 |
| Sodium hydrogensulfite | 0.01 |
| Ethylparaben | 0.3 |
| Carboxyvinyl polymer | 0.05 |
| Perfume | q.s. |
| Ion exchanged water | balance |

Manufacturing Method

The preparation with respect to the present example was prepared by the same method described in the explanation of example 7.

| EXAMPLE 30 MILKY LOTION | weight % |
|---|---|
| Oil phase: | |
| Stearyl alcohol | 1.5 |
| Squalene | 2.0 |
| Petrolatum | 2.5 |
| Deodorized liquid lanoline | 1.5 |
| Evening primrose oil | 2.0 |
| Isopropyl myristate | 5.0 |
| Glycerine monoleate | 2.0 |
| Polyoxyethylene (60 moles) hydrogenated castor oil | 2.0 |
| Tocopherol acetate | 0.05 |
| Ethylparaben | 0.2 |
| Butylparaben | 0.1 |
| L-phenylalanyl-trans-4-aminomethylcyclohexane carboxylic acid | 1.0 |
| L-isoleusyl-trans-4-aminomethylcyclohexane carboxylic acid hydrochloride | 1.0 |
| Perfume | q.s. |
| Aqueous phase: | |
| Sodium hydrogensulfite | 0.01 |
| Glycerol | 5.0 |
| Sodium hyaluronate | 0.01 |
| Carboxyvinyl polymer | 0.2 |
| Potassium hydroxide | 0.2 |
| Purified water | balance |

Manufacturing Method

The preparation with respect to the present example was prepared by the same method described in the explanation of example 8.

| EXAMPLE 31 JELLY | weight % |
|---|---|
| 95% ethyl alcohol | 10.0 |
| Dipropyleneglycol | 15.0 |
| Polyoxyethylene (50 moles) oleylalcohol ether | 2.0 |
| Carboxyvinyl polymer | 1.0 |
| Caustic soda | 0.15 |
| L-arginine | 0.1 |
| L-seryl-trans-4-aminomethylcyclohexane | 1.0 |

| EXAMPLE 31 JELLY | weight % |
|---|---|
| carboxylic acid hydrochloride | |
| L-tyrosyl-trans-4-aminomethylcyclohexanecarboxylic acid | 1.0 |
| 4-hydroxybenzoic acid methylester | 0.2 |
| Perfume | q.s. |
| Ion exchanged water | balance |

Manufacturing Method

The preparation with respect to the present example was prepared by the same method described in the explanation of example 9.

| EXAMPLE 32 LOTION | weight % |
|---|---|
| A phase: | |
| Ethanol (95%) | 10.0 |
| Polyoxyethylene (20 moles) octyldodecanol | 1.0 |
| 4-hydroxybenzoic acid methylester | 0.15 |
| Pantothenyl ethyl ether | 0.1 |
| L-lysyl-trans-4-aminomethylcyclohexanecarboxylic acid | 0.05 |
| B phase: | 0.1 |
| Potassium hydroxide | |
| C phase: | |
| Glycerol | 5.0 |
| Dipropyleneglycol | 10.0 |
| Sodium hydrogensulfite | 0.03 |
| Carboxyvinyl polymer | 0.2 |
| Purified water | balance |

Manufacturing Method

The preparation with respect to the present example was prepared by the same method described in the explanation of example 10.

| EXAMPLE 33 PACK | weight % |
|---|---|
| A phase: | |
| Dipropyleneglycol | 5.0 |
| Polyoxyethylene (60 moles) hydrogenated castor oil | 5.0 |
| B phase: | |
| L-asparaginyl-trans-4-aminomethylcyclohexane carboxylic acid | 1.0 |
| L-glutamyl-trans-4-aminomethylcyclohexanecarboxylic acid | 1.0 |
| Olive oil | 5.0 |
| Tocopherol acetate | 0.2 |
| Ethylparaben | 0.2 |
| Perfume | 0.2 |
| C phase: | |
| Sodium hydrogensulfite | 0.03 |
| Polyvinyl alcohol (saponification degree 90, degree of polymerization 2000) | 13.0 |
| Ethanol | 7.0 |
| Purified water | balance |

Manufacturing Method

The preparation with respect to the present example was prepared by the same method described in the explanation of example 11.

COMPOUND GROUP 4

(1) Depigmentation Effect

The depigmentation effect of the compound group 3 was examined according to the method described above.

The results are shown in TABLE 7.

TABLE 7

| | COMPOUND | DEPIGMENTATION EFFECT |
|---|---|---|
| COMPARISON 1 | NONE | x |
| COMPARISON 2 | HYDROQUINONE | △ |
| EXAMPLE 34 | Trans-4-ethylaminomethyl cyclohexanecarboxylic acid hydrochloride | ⊙ |
| EXAMPLE 35 | Trans-4-diethylaminomethyl-cyclohexane carboxylic acid | ⊙ |
| EXAMPLE 36 | Trans-4-diisobutylamino-methyl cyclohexanecarboxylic acid hydrochloride | ⊙ |

As is clear from TABLE 7, the external preparation for the skin according to the Examples 34 to 36 could also suppress deposition of melanoic pigment and suntan.

(2) Skin Care Effect

The skin care effect of the compound group 3 was examined according to the method described above.

The results are shown in TABLE 8.

TABLE 8

| | moisturising effect | texture of skin surface | maintenance of moisturising effect |
|---|---|---|---|
| COMPARISON 1 | x | x | x |
| EXAMPLE 34 | ⊙ | ⊙ | ⊙ |
| EXAMPLE 35 | ⊙ | ⊙ | ⊙ |
| EXAMPLE 36 | ⊙ | ⊙ | ⊙ |

As is clear from TABLE 8, the external preparation for the skin according to the Examples 34 to 36 had excellent skin care effect.

| EXAMPLE 37 CREAM | weight % |
|---|---|
| Stearic acid | 5.0 |
| Stearyl alcohol | 4.0 |
| Isopropyl myristate | 18.0 |
| Glycerine mono stearate | 3.0 |
| Propylene glycol | 10.0 |
| Trans-4-methylaminomethylcyclohexanecarboxylic acid hydrochloride | 20.0 |
| Caustic potash | 0.2 |
| Sodium hydrogensulfite | 0.01 |
| Antiseptic | q.s. |
| Perfume | q.s. |
| Ion exchanged water | balance |

Manufacturing Method

The preparation with respect to the present example was prepared by the same method described in the explanation of example 4.

| EXAMPLE 38 CREAM | weight % |
|---|---|
| Stearic acid | 6.0 |
| Sorbitane monostearate | 2.0 |
| Polyoxyethylene (20 moles) sorbitanemonostearate | 1.5 |
| Propylene glycol | 10.0 |
| Trans-4-methylaminomethylcyclohexanecarboxylic acid | 7.0 |

| EXAMPLE 38 CREAM | weight % |
| --- | --- |
| Glycerine trioctanoate | 10.0 |
| Squalene | 5.0 |
| Sodium hydrogensulfite | 0.01 |
| Ethylparaben | 0.3 |
| Perfume | q.s. |
| Ion exchanged water | balance |

Manufacturing Method

The preparation with respect to the present example was prepared by the same method described in the explanation of example 5.

| EXAMPLE 39 CREAM | weight % |
| --- | --- |
| Stearyl alcohol | 7.0 |
| Stearic acid | 2.0 |
| Hydrogenated lanoline | 2.0 |
| Squalane | 5.0 |
| 2-octyldodesylalcohol | 6.0 |
| Polyoxyethylene (25 moles) cetyl alcohol ether | 3.0 |
| Glycerinemonostearate | 2.0 |
| Propylene glycol | 5.0 |
| Trans-4-ethylaminomethylcyclohexanecarboxylic acid | 0.005 |
| Perfume | q.s. |
| Sodium hydrogensulfite | 0.03 |
| Ethylparaben | 0.3 |
| Ion exchanged water | balance |

Manufacturing Method

The preparation with respect to the present example was prepared by the same method described in the explanation of example 6.

| EXAMPLE 29 MILKY LOTION | weight % |
| --- | --- |
| Stearic acid | 2.5 |
| Cetyl alcohol | 1.5 |
| Petrolatum | 5.0 |
| Liquid paraffin | 10.0 |
| Polyoxyethylene (10 moles) monoleate | 2.0 |
| Polyethylene glycol 1500 | 3.0 |
| Triethanolamine | 1.0 |
| Trans-4-dimethylaminomethylcyclohexanecarboxylic acid | 10.0 |
| Sodium hydrogensulfite | 0.01 |
| Ethylparaben | 0.3 |
| Carboxyvinyl polymer | 0.05 |
| Perfume | q.s. |
| Ion exchanged water | balance |

Manufacturing Method

The preparation with respect to the present example was prepared by the same method described in the explanation of example 7.

| EXAMPLE 41 MILKY LOTION | weight % |
| --- | --- |
| Oil Phase: | |
| Stearyl alcohol | 1.5 |
| Squalene | 2.0 |
| Petrolatum | 2.5 |
| Deodorized liquid lanoline | 1.5 |
| Evening primrose oil | 2.0 |

| EXAMPLE 41 MILKY LOTION | weight % |
| --- | --- |
| Isopropyl myristate | 5.0 |
| Glycerine monoleate | 2.0 |
| Polyoxyethylene (60 moles) hydrogenated castor oil | 2.0 |
| Tocopherol acetate | 0.05 |
| Ethylparaben | 0.2 |
| Butylparaben | 0.1 |
| Trans-4-diethylaminomethylcyclohexane carboxylic acid hydrochloride | 1.0 |
| Trans-4-ethylaminomethylcyclohexanecarboxylic acid | 1.0 |
| Perfume | q.s. |
| Aqueous Phase: | |
| Sodium hydrogensulfite | 0.01 |
| Glycerol | 5.0 |
| Sodium hyaluronate | 0.01 |
| Carboxyvinyl polymer | 0.2 |
| Potassium hydroxide | 0.2 |
| Purified water | balance |

Manufacturing Method

The preparation with respect to the present example was prepared by the same method described in the explanation of example 8.

| EXAMPLE 42 JELLY | weight % |
| --- | --- |
| 95% ethyl alcohol | 10.0 |
| Dipropyleneglycol | 15.0 |
| Polyoxyethylene (50 moles) oleyl alcohol ether | 2.0 |
| Carboxyvinyl polymer | 1.0 |
| Caustic soda | 0.15 |
| L-arginine | 0.1 |
| Trans-4-methylaminomethylcyclohexane carboxylic acid hydrochloride | 1.0 |
| Trans-4-dimethylaminomethylcyclohexane carboxylic acid | 1.0 |
| 4-hydroxybenzoic acid methylester | 0.2 |
| Perfume | q.s. |
| Ion echanged water | balance |

Manufacturing Method

The preparation with respect to the present example was prepared by the same method described in the explanation of example 9.

| EXAMPLE 43 LOTION | weight % |
| --- | --- |
| A Phase: | |
| Ethanol (95%) | 10.0 |
| Polyoxyethylene (20 moles) octyldodecanol | 1.0 |
| 4-hydroxybenzoic acid methylester | 0.15 |
| Pantothenyl ethyl ether | 0.1 |
| Trans-4-diethylaminomethylcyclohexanecarboxylic acid hydrochloride | 0.05 |
| B Phase: | |
| Potassium hydroxide | 0.1 |
| C Phase: | |
| Glycerol | 5.0 |
| Dipropyleneglycol | 10.0 |
| Sodium hydrogensulfite | 0.03 |
| Carboxyvinyl polymer | 0.2 |
| Purified water | balance |

Manufacturing Method

The preparation with respect to the present example was prepared by the same method described in the explanation of example 10.

| EXAMPLE 44 PACK | weight % |
| --- | --- |
| A Phase: | |
| Dipropyleneglycol | 5.0 |
| Polyoxyethylene (60 moles) hydrogenated castor oil | 5.0 |
| B Phase: | |
| Trans-4-dimethylaminomethylcyclohexane carboxylic acid hydrochloride | 1.0 |
| Trans-4-diethylaminomethylcyclohexane carboxylic acid hydrochloride | 1.0 |
| Olive oil | 5.0 |
| Tocopherol acetate | 0.2 |
| Ethylparaben | 0.2 |
| Perfume | 0.2 |
| C Phase: | |
| Sodium hydrogensulfite | 0.03 |
| Polyvinyl alcohol (saponification degree 90, degree of polymerization 2000) | 13.0 |
| Ethanol | 7.0 |
| Purified water | balance |

Manufacturing Method

The preparation with respect to the present example was prepared by the same method described in the explanation of example 11.

COMPOUND GROUP 5

(1) Depigmentation Effect

The depigmentation effect of the compound group 5 was examined according to the method described above.

The result is shown in TABLE 9.

TABLE 9

| | COMPOUND | DEPIGMENTATION EFFECT |
| --- | --- | --- |
| COMPARISON 1 | NONE | x |
| COMPARISON 2 | HYDROQUINONE | Δ |
| EXAMPLE 45 | Trans-4-ureidomethyl cyclohexanecarboxylic acid | ⊚ |
| EXAMPLE 46 | Trans-4-(N'-ethylureido-methyl) cyclohexane carboxylic acid | ⊚ |
| EXAMPLE 47 | Trans-4-(N'-cyclohexylureido-methyl) cyclohexane-carboxylic acid | ⊚ |

As is clear from TABLE 9, the external preparation for the skin according to the Examples 45 to 47 could also suppress deposition of melanoic pigment and suntan.

(2) Skin Care Effect

The skin care effect of the compound group 3 was examined according to the method described above.

The results are shown in TABLE 10.

TABLE 10

| | moisturising effect | texture of skin surface | maintenance of moisturising effect |
| --- | --- | --- | --- |
| COMPARISON 1 | x | x | x |
| EXAMPLE 45 | ⊚ | ⊚ | ⊚ |
| EXAMPLE 46 | ⊚ | ⊚ | ⊚ |
| EXAMPLE 47 | ⊚ | ⊚ | ⊚ |

As is clear from TABLE 10, the external preparation for the skin according to Examples 45 to 47 had excellent skin care effect.

| EXAMPLE 48 CREAM | weight % |
| --- | --- |
| Stearic acid | 5.0 |
| Stearyl alcohol | 4.0 |
| Isopropyl myristate | 18.0 |
| Glycerine mono stearate | 3.0 |
| Propylene glycol | 10.0 |
| Trans-4-(N'-n-butylureidomethyl)cyclohexane carboxylic acid | 20.0 |
| Caustic potash | 0.2 |
| Sodium hydrogensulfite | 0.01 |
| Antiseptic | q.s. |
| Perfume | q.s. |
| Ion exchanged water | balance |

Manufacturing Method

The preparation with respect to the present example was prepared by the same method described in the explanation of example 4.

| EXAMPLE 49 CREAM | weight % |
| --- | --- |
| Stearic acid | 6.0 |
| Sorbitane monostearate | 2.0 |
| Polyoxyethylene (20 moles) sorbitanemonostearate | 1.5 |
| Propylene glycol | 10.0 |
| Trans-4-(N'-ethoxycarbonylmethylureidomethyl) cyclohexanecarboxylic acid | 7.0 |
| Glycerine trioctanoate | 10.0 |
| Squalene | 5.0 |
| Sodium hydrogensulfite | 0.01 |
| Ethylparaben | 0.3 |
| Perfume | q.s. |
| Ion exchanged water | balance |

Manufacturing Method

The preparation with respect to the present example was prepared by the same method described in the explanation of example 5.

| EXAMPLE 50 CREAM | weight % |
| --- | --- |
| Stearyl alcohol | 7.0 |
| Stearic acid | 2.0 |
| Hydrogenated lanoline | 2.0 |
| Squalane | 5.0 |
| 2-octyldodesylalcohol | 6.0 |
| Polyoxyethylene (25 moles) cetyl alcohol ether | 3.0 |
| Glycerinemonostearate | 2.0 |
| Propylene glycol | 5.0 |
| Trans-4-(N'-phenylureidomethyl) cyclohexanecarboxylic acid | 0.005 |

| EXAMPLE 50 CREAM | weight % |
| --- | --- |
| Perfume | q.s. |
| Sodium hydrogensulfite | 0.03 |
| Ethylparaben | 0.3 |
| Ion exchanged water | balance |

Manufacturing Method

The preparation with respect to the present example was prepared by the same method described in the explanation of example 6.

| EXAMPLE 51 MILKY LOTION | weight % |
| --- | --- |
| Stearic acid | 2.5 |
| Cetyl alcohol | 1.5 |
| Petrolatum | 5.0 |
| Liquid paraffin | 10.0 |
| Polyoxyethylene (10 moles) monooleate | 2.0 |
| Polyethylene glycol 1500 | 3.0 |
| Triethanolamine | 1.0 |
| Trans-4-(N'-2'-chlorophenylureidomethyl)cyclohexanecarboxylic acid | 10.0 |
| Sodium hydrogensulfite | 0.01 |
| Ethylparaben | 0.3 |
| Carboxyvinyl polymer | 0.05 |
| Perfume | q.s. |
| Ion exchanged water | balance |

Manufacturing Method

The preparation with respect to the present example was prepared by the same method described in the explanation of example 7.

| EXAMPLE 52 MILKY LOTION | weight % |
| --- | --- |
| Oil phase: | |
| Stearyl alcohol | 1.5 |
| Squalene | 2.0 |
| Petrolatum | 2.5 |
| Deodorized liquid lanoline | 1.5 |
| Evening primrose oil | 2.0 |
| Isopropyl myristate | 5.0 |
| Glycerine monooleate | 2.0 |
| Polyoxyethylene (60 moles) hydrogenated castor oil | 2.0 |
| Tocopherol acetate | 0.05 |
| Ethylparaben | 0.2 |
| Butylparaben | 0.1 |
| Trans-4-ureidomethylcyclohexanecarboxylic acid | 1.0 |
| Trans-4-(N'-ethylureidomethyl)cyclohexanecarboxylic acid | 1.0 |
| Perfume | q.s. |
| (Aqueous phase) | |
| Sodium hydrogensulfite | 0.01 |
| Glycerol | 5.0 |
| Sodium hyaluronate | 0.01 |
| Carboxyvinyl polymer | 0.2 |
| Potassium hydroxide | 0.2 |
| Purified water | balance |

Manufacturing Method

The preparation with respect to the present example was prepared by the same method described in the explanation of example 8.

| EXAMPLE 53 JELLY | weight % |
| --- | --- |
| 95% ethyl alcohol | 10.0 |
| Propyleneglycol | 15.0 |
| Polyoxyethylene (50 moles) oleyl alcohol ether | 2.0 |
| Carboxyvinyl polymer | 1.0 |
| Caustic soda | 0.15 |
| L-arginine | 0.1 |
| Trans-4-(N'-n-butylureidomethyl)cyclohexane carboxylic acid | 1.0 |
| Trans-4-(N'-ethoxycarbonylmethylureidomethyl)cyclohexanecarboxylic acid | 1.0 |
| 4-hydroxybenzoic acid methylester | 0.2 |
| Perfume | q.s. |
| Ion exchanged water | balance |

Manufacturing Method

The preparation with respect to tim present example was prepared by the same method described in the explanation of example 9.

| EXAMPLE 54 LOTION | weight % |
| --- | --- |
| A phase: | |
| Ethanol (95%) | 10.0 |
| Polyoxyethylene (50 moles) octyldodecanol | 1.0 |
| 4-hydroxybenzoic acid methylester | 0.15 |
| Pantothenyl ethyl ether | 0.1 |
| Trans-4-(N'-cyclohexylureidomethyl)cyclohexane carboxylic acid | 0.05 |
| B phase: | 0.1 |
| Potassium hydroxide | |
| C phase: | |
| Glycerol | 5.0 |
| Dipropyleneglycol | 10.0 |
| Sodium hydrogensulfite | 0.03 |
| Carboxyvinyl polymer | 0.2 |
| Purified water | balance |

Manufacturing Method

The preparation with respect to the present example was prepared by the same method described in the explanation of example 10.

| EXAMPLE 55 PACK | weight % |
| --- | --- |
| A phase: | |
| Dipropyleneglycol | 5.0 |
| Polyoxyethylene (60 moles) hydrogenated castor oil | 5.0 |
| B phase: | |
| Trans-4-(N'-phenylureidomethyl)cyclohexanecarboxylic acid | 1.0 |
| Trans-4-(N'-2'-chlorophenylureidomethyl)cyclohexane carboxylic acid | 1.0 |
| Olive oil | 5.0 |
| Tocopherol acetate | 0.2 |
| Ethylparaben | 0.2 |
| Perfume | 0.2 |
| C phase: | |
| Sodium hydrogensulfite | 0.03 |
| Polyvinyl alcohol (saponification degree 90, degree of polymerization 2000) | 13.0 |
| Ethanol | 7.0 |
| Purified water | balance |

Manufacturing Method

The preparation with respect to the present example was prepared by the same method described in the explanation of example 11.

COMPOUND GROUP 6

(1) Depigmentation Effect

The depigmentation effect of the compound group 6 was examined according to the method described above.

The result is shown in TABLE 11.

TABLE 11

|  | COMPOUN | DEPIGMENTATION EFFECT |
|---|---|---|
| COMPARISON 1 | NONE | x |
| COMPARISON 2 | HYDROQUINONE | △ |
| EXAMPLE 56 | Trans-4-guanidinomethyl cyclohexanecarboxylicacid | ⊙ |
| EXAMPLE 57 | Ethyltrans-4-guanidinomethyl cyclohexanecarboxylate hydrochloride | ⊙ |
| EXAMPLE 58 | Octane-2-yl-trans-4-guani- dinomethyl cyclohexane- carboxylate hydrochloride | ⊙ |

As is clear from TABLE 11, the external preparation for the skin according to Examples 56 to 58 could also suppress deposition of melanoic pigment and suntan.

(2) Skin Care Effect

The skin care effect of the compound group 6 was examined according to the method described above.

The results are shown in TABLE 12.

TABLE 12

|  | moisturising effect | texture of skin surface | maintenance of moisturising effect |
|---|---|---|---|
| COMPARISON 1 | x | x | x |
| EXAMPLE 56 | ⊙ | ⊙ | ⊙ |
| EXAMPLE 57 | ⊙ | ⊙ | ⊙ |
| EXAMPLE 58 | ⊙ | ⊙ | ⊙ |

As is clear from TABLE 12, the external preparation for the skin according to Examples 56 to 58 had excellent skin care effect.

| EXAMPLE 59 CREAM | weight % |
|---|---|
| Stearic acid | 5.0 |
| Stearyl alcohol | 4.0 |
| Isopropyl myristate | 18.0 |
| Glycerine mono stearate | 3.0 |
| Propylene glycol | 10.0 |
| Benzyltrans-4-guanidinomethylcyclohexane carboxylate hydrochoride | 20.0 |
| Caustic potash | 0.2 |
| Sodium hydrogensulfite | 0.01 |
| Antiseptic | q.s. |
| Perfume | q.s. |
| Ion exchanged water | balance |

Manufacturing Method

The preparation with respect to the present example was prepared by the same method described in the explanation of example 4.

| EXAMPLE 60 CREAM | weight % |
|---|---|
| Stearic acid | 6.0 |
| Sorbitane monostearate | 2.0 |
| Polyoxyethylene (20 moles) sorbitanemonostearate | 1.5 |
| Propylene glycol | 10.0 |
| 4'-pyridylmethyltrans-4-guanidinomethyl cyclohexanecarboxylate hydrochloride | 7.0 |
| Glycerine trioctanoate | 10.0 |
| Squalene | 5.0 |
| Sodium hydrogensulfite | 0.01 |
| Ethylparaben | 0.3 |
| Perfume | q.s. |
| Ion exchanged waer | balance |

Manufacturing Method

The preparation with respect to the present example was prepared by the same method described in the explanation of example 5.

| EXAMPLE 61 CREAM | weight % |
|---|---|
| Stearyl alcohol | 7.0 |
| Stearic acid | 2.0 |
| Hydrogenated lanoline | 2.0 |
| Squalane | 5.0 |
| 2-octyldodesylalcohol | 6.0 |
| Polyoxyethylene (25 moles) cetyl alcohol ether | 3.0 |
| Glycerinemonostearate | 2.0 |
| Propylene glycol | 5.0 |
| Cyclohexyltrans-4-guanidinomethyl cyclohexanecarboxylate hydrochloride | 0.005 |
| Perfume | q.s. |
| Sodium hydrogensulfite | 0.03 |
| Ethylparaben | 0.3 |
| Ion exchanged water | balance |

Manufacturing Method

The preparation with respect to the present example was prepared by the same method described in the explanation of example 6.

| EXAMPLE 62 MILKY LOTION | weight % |
|---|---|
| Stearic acid | 2.5 |
| Cetyl alcohol | 1.5 |
| Petrolatum | 5.0 |
| Liquid paraffin | 10.0 |
| Polyoxyethylene (10 moles) monoleate | 2.0 |
| Polyethylene glycol 1500 | 3.0 |
| Triethanolamine | 1.0 |
| Trans-4-guanidinomethylcyclohexanecarboxylic acid hydrochloride | 10.0 |
| Sodium hydrogensulfite | 0.01 |
| Ethylparaben | 0.3 |
| Carboxyvinyl polymer | 0.05 |
| Perfume | q.s. |
| Ion exchanged water | balance |

Manufacturing Method

The preparation with respect to the present example was prepared by the same method described in the explanation of example 7.

| EXAMPLE 63 MILKY LOTION | weight % |
| --- | --- |
| Oil phase: | |
| Stearyl alcohol | 1.5 |
| Squalene | 2.0 |
| Petrolatum | 2.5 |
| Deodorized liquid lanoline | 1.5 |
| Evening primrose oil | 2.0 |
| Isopropyl myristate | 5.0 |
| Glycerine monooleate | 2.0 |
| Polyoxyethylene (60 moles) hydrogenated castor oil | 2.0 |
| Tocopherol acetate | 0.05 |
| Ethylparaben | 0.2 |
| Butylparaben | 0.1 |
| Ethyltrans-4-guanidinomethylcyclohexanecarboxylate hydrochloride | 1.0 |
| Benzyltrans-4-guanidinomethylcyclohexanecarboxylate hydrochloride | 1.0 |
| Perfume | q.s. |
| Aqueous phase: | |
| Sodium hydrogensulfite | 0.01 |
| Glycerol | 5.0 |
| Sodium hyaluronate | 0.01 |
| Carboxyvinyl polymer | 0.2 |
| Potassium hydroxide | 0.2 |
| Purified water | balance |

Manufacturing Method

The preparation with respect to the present example was prepared by the same method described in the explanation of example 8.

| EXAMPLE 64 JELLY | weight % |
| --- | --- |
| 95% ethyl alcohol | 10.0 |
| Dipropyleneglycol | 15.0 |
| Polyoxyethylene (50 moles) oleylalcohol ether | 2.0 |
| Carboxyvinyl polymer | 1.0 |
| Caustic soda | 0.15 |
| L-arginine | 0.1 |
| Octan-2-yl-trans-4-guanidinomethylcyclohexane carboxylate hydrochloride | 1.0 |
| Cyclohexyltrans-4-guanidinomethyl cyclohexanecarboxylate hydrochloride | 1.0 |
| 4-hydroxybenzoic acid methylester | 0.2 |
| perfume | q.s. |
| Ion exchanged water | balance |

Manufacturing Method

The preparation with respect to the present example was prepared by the same method described in the explanation of example 9.

| EXAMPLE 65 LOTION | weight % |
| --- | --- |
| A phase: | |
| Ethanol (95%) | 10.0 |
| Polyoxyethylene (20 moles) octyldodecanol | 1.0 |
| 4-hydroxybenzoic acid methylester | 0.15 |
| Pantothenyl ethyl ether | 0.1 |
| Ethyltrans-4-guanidinomethylcyclohexane carboxylate hydrochloride | 0.05 |
| B phase: | |
| Potassium hydroxide | 0.1 |
| C phase: | |
| Glycerol | 5.0 |

-continued

| EXAMPLE 65 LOTION | weight % |
| --- | --- |
| Dipropyleneglycol | 10.0 |
| Sodium hydrogensulfite | 0.03 |
| Carboxyvinyl polymer | 0.2 |
| Purified water | balance |

Manufacturing Method

The preparation with respect to the present example was prepared by the same method described in the explanation of example 10.

| EXAMPLE 66 PACK | weight % |
| --- | --- |
| A phase: | |
| Dipropyleneglycol | 5.0 |
| Polyoxyethylene (60 moles) hydrogenated castor oil | 5.0 |
| B phase: | |
| Ethyltrans-4-guanidinomethyl cyclohexanecarboxylate hydrochloride | 1.0 |
| Trans-4-guanidinomethylcyclohexane carboxylic acid hydrochloride | 1.0 |
| Olive oil | 5.0 |
| Tocopherol acetate | 0.2 |
| Ethylparaben | 0.2 |
| C phase: | |
| Sodium hydrogensulfite | 0.03 |
| Polyvinyl alcohol (saponification degree 90, degree of polymerization 2000) | 13.0 |
| Ethanol | 7.0 |
| Purified water | balance |

Manufacturing Method

The preparation with respect to the present example was prepared by the same method described in the explanation of example 11.

COMPOUND GROUP 7

(1) Depigmentation

The depigmentation effect of the compound group 7 was examined according to the method described above.

The result is shown in TABLE 13.

TABLE 13

| | COMPOUND | DEPIGMENTATION EFFECT |
| --- | --- | --- |
| COMPARISON 1 | NONE | x |
| COMPARISON 2 | HYDROQUINONE | △ |
| EXAMPLE 67 | Trans-4-guanidinomethyl-cyclohexanecarboxylic acid 3'-carboxyphenyl ester hydrochloride | ⊙ |
| EXAMPLE 68 | Trans-4-guanidinomethyl-cyclohexanecarboxylic acid 4'-phenoxycarbonylphenyl-ester hydrochloride | ⊙ |
| EXkMPLE 69 | Trans-4-guanidinomethyl-cyclohexanecarboxylic acid 4'-ethoxycarbonylphenyl-ester hydrochloride | ⊙ |

As is clear from TABLE 13, the external preparation for the skin according to Examples 67 to 69 could also suppress deposition of melanoic pigment and suntan.

(2) Skin Care Effect

The skin care effect of the compound group 7 was examined according to the method described above. The results are shown in TABLE 14.

TABLE 14

|  | moisturising effect | texture of skin surface | maintenance of moisturising effect |
| --- | --- | --- | --- |
| COMPARISON 1 | x | x | x |
| EXAMPLE 67 | ⊚ | ⊚ | ⊚ |
| EXAMPLE 68 | ⊚ | ⊚ | ⊚ |
| EXAMPLE 69 | ⊚ | ⊚ | ⊚ |

As is clear from TABLE 14, the external preparation for the skin according to Examples 67 to 69 had excellent skin care effect.

| EXAMPLE 70 CREAM | weight % |
| --- | --- |
| Stearic acid | 5.0 |
| Stearyl alcohol | 4.0 |
| Isopropyl myristate | 18.0 |
| Glycerine monostearate | 3.0 |
| Propylene glycol | 10.0 |
| Trans-4-guanidinomethylcyclohexanecarboxylic acid 3'-Benzyloxycarbonylphenylester hydrochloride | 20.0 |
| Caustic potash | 0.2 |
| Sodium hydrogensulfite | 0.01 |
| Antiseptic | q.s. |
| Perfume | q.s. |
| Ion exchanged water | balance |

Manufacturing Method

The preparation with respect to the present example was prepared by the same method described in the explanation of example 4.

| EXAMPLE 71 CREAM | weight % |
| --- | --- |
| Stearic acid | 6.0 |
| Sorbitane monostearate | 2.0 |
| Polyoxyethylene (20 moles) sorbitanemonostearate | 1.5 |
| Propylene glycol | 10.0 |
| Trans-4-guanidinomethylcyclohexanecarboxylic acid 4'-(2-carboxyethyl)phenylester hydrochloride | 7.0 |
| Glycerine trioctanoate | 10.0 |
| Squalene | 5.0 |
| Sodium hydrogensulfite | 0.01 |
| Ethylparaben | 0.3 |
| Perfume | q.s. |
| Ion exchanged water | balance |

Manufacturing Method

The preparation with respect to the present example was prepared by the same method described in the explanation of example 5.

| EXAMPLE 72 CREAM | weight % |
| --- | --- |
| Stearyl alcohol | 7.0 |
| Stearic acid | 2.0 |
| Hydrogenated lanoline | 2.0 |
| Squalane | 5.0 |
| 2-octyldodesylalcohol | 6.0 |
| Polyoxyethylene (25 moles) cetyl alcohol ether | 3.0 |
| Glycerinemonostearate | 2.0 |
| Propylene glycol | 5.0 |
| Trans-4-guanidinomethylcyclohexanecarboxylic acid 4'-(2-ethoxycarbonylethyl) phenylester hydrochloride | 0.005 |
| Perfume | q.s. |
| Sodium hydrogensulfite | 0.03 |
| Ethylparaben | 0.3 |
| Ion exchanged water | balance |

Manufacturing Method

The preparation with respect to the present example was prepared by the same method described in the explanation of example 6.

| EXAMPLE 73 MILKY LOTION | weight % |
| --- | --- |
| Stearic acid | 2.5 |
| Cetyl alcohol | 1.5 |
| Petrolatum | 5.0 |
| Liquid paraffin | 10.0 |
| Polyoxyethylene (10 moles) monoleate | 2.0 |
| Polyethylene glycol 1500 | 3.0 |
| Triethanolamine | 1.0 |
| Trans-4-guanidinomethylcyclohexanecarboxylic acid 4'-carboxymethylphenylester hydrochloride | 10.0 |
| Sodium hydrogensulfite | 0.01 |
| Ethyl paraben | 0.3 |
| Carboxyvinyl polymer | 0.05 |
| Perfume | q.s. |
| Ion exchanged water | balance |

Manufacturing Method

The preparation with respect to the present example was prepared by the same method described in the explanation of example 7.

| EXAMPLE 74 MILKY LOTION | weight % |
| --- | --- |
| Oil phase: | |
| Stearyl alcohol | 1.5 |
| Squalene | 2.0 |
| Petrolatum | 2.5 |
| Deodorized liquid lanoline | 1.5 |
| Evening primrose oil | 2.0 |
| Isopropyl myristate | 5.0 |
| Glycerine monoleate | 2.0 |
| Polyoxyethylene (60 moles) hydrogenated castor oil | 2.0 |
| Tocopherol acetate | 0.05 |
| Ethylparaben | 0.2 |
| Butylparaben | 0.1 |
| Trans-4-guanidinomethylcyclohexanecarboxylic acid 4'-benzyloxycarbonylphenylester hydrochloride | 1.0 |
| Trans-4-guanidinomethylcyclohexanecarboxylic acid 3'-methoxycarbonylphenylester hydrochloride | 1.0 |
| Perfume | q.s. |
| Aqueous phase: | |
| Sodium hydrogensulfite | 0.01 |
| Glycerol | 5.0 |
| Sodium hyaluronate | 0.01 |
| Carboxyvinyl polymer | 0.2 |
| Potassium hydroxide | 0.2 |
| Purified water | balance |

Manufacturing Method

The preparation with respect to the present example was prepared by the same method described in the explanation of example 8.

| EXAMPLE 75 JELLY | weight % |
| --- | --- |
| 95% ethyl alcohol | 10.0 |
| Dipropyleneglycol | 15.0 |
| Polyoxyethylene (50 moles) oleyl alcohol ether | 2.0 |
| Carboxyvinyl polymer | 1.0 |
| Caustic soda | 0.15 |
| L-arginine | 0.1 |
| Trans-4-guanidinomethylcyclohexanecarboxylic acid 4'-t-butyloxycarbonylmethylphanylester hydrochloride | 0.05 |
| Trans-4-guanidinomethylcyclohexanecarboxylic acid 4'-carboxyphenylester hydrochloride | 1.0 |
| 4-hydroxybenzoic acid methylester | 0.2 |
| Perfume | q.s. |
| Ion exchanged water | balance |

Manufacturing Method

The preparation with respect to the present example was prepared by the same method described in the explanation of example 9.

| EXAMPLE 76 LOTION | weight % |
| --- | --- |
| A phase: | |
| Ethanol (95%) | 10.0 |
| Polyoxyethylene (20 moles) octyldodecanol | 1.0 |
| 4-hydroxybenzoic acid methylester | 0.15 |
| Pantothenyl ethyl ether | 0.1 |
| Trans-4-guanidinomethylcyclohexanecarboxylic acid 4'-ethoxycarbonylphenylester hydrochloride | 0.05 |
| B phase: | 0.1 |
| Potassium hydroxide | |
| C phase: | |
| Glycerol | 5.0 |
| dipropyleneglycol | 10.0 |
| Sodium hydrogensulfite | 0.03 |
| Carboxyvinyl polymer | 0.2 |
| Purified water | balance |

Manufacturing Method

The preparation with respect to the present example was prepared by the same method described in the explanation of example 10.

| EXAMPLE 77 PACK | weight % |
| --- | --- |
| A phase: | |
| Dipropyleneglycol | 5.0 |
| Polyoxyethylene (60 moles) hydrogenated castor oil | 5.0 |
| B phase: | |
| Trans-4-guanidinomethylcyclohexanecarboxylic acid 4'-phenoxycarbonylphenylester hydrochloride | 1.0 |
| Trans-4-guanidinomethylcyclohexanecarboxylic acid 4'-(2-carboxyethyl)phenylester hydrochloride | 1.0 |
| Olive oil | 5.0 |
| Tocopherol acetate | 0.2 |
| Ethylparaben | 0.2 |
| Perfume | 0.2 |

| EXAMPLE 77 PACK | weight % |
| --- | --- |
| C phase: | |
| Sodium hydrogensulfite | 0.03 |
| Polyvinyl alcohol (saponification degree 90 degree of polymerization 2000) | 13.0 |
| Ethanol | 7.0 |
| Purified water | balance |

Manufacturing Method

The preparation with respect to the present example was prepared by the same method described in the explanation of example 11.

COMPOUND GROUP 8

(1) Depigmentation Effect

The depigmentation effect of the compound group 8 was examined according to the method described above.

The results are shown in TABLE 15.

TABLE 15

| | COMPOUND | DEPIGMENTATION EFFECT |
| --- | --- | --- |
| COMPARISON 1 | NONE | x |
| COMPARISON 2 | HYDROQUINONE | Δ |
| EXAMPLE 78 | Trans-4-guanidinomethyl-cyclohexanecarboxylic acid phenyl ester hydrochloride | ⊚ |
| EXAMPLE 19 | Trans-4-guanidinomethyl-cyclohexanecarboxylic acid 4'-ethylphenylester hydrochloride | ⊚ |
| EXAMPLE 80 | Trans-4-guanidinomethyl-cyclohexanecarboxylic acid 2'-methoxyphenylester hydrochloride ⊚ | ⊚ |

As is clear from TABLE 15, the external preparation for the skin according to Examples 78 to 80 could also suppress deposition of melanoic pigment and suntan.

(2) Skin Care Effect

The skin care effect of the compound group 8 was examined according to the method described above.

The results are shown in TABLE 16.

TABLE 16

| | moisturising effect | texture of skin surface | maintenance of moisturising effect |
| --- | --- | --- | --- |
| COMPARISON 1 | x | x | x |
| EXAMPLE 78 | ⊚ | ⊚ | ⊚ |
| EXAMPLE 79 | ⊚ | ⊚ | ⊚ |
| EXAMPLE 80 | ⊚ | ⊚ | ⊚ |

As is clear from TABLE 16, the external preparation for the skin according to Examples 78 to 80 had excellent skin care effect.

| EXAMPLE 81 CREAM | weight % |
|---|---|
| Stearic acid | 5.0 |
| Stearyl alcohol | 4.0 |
| Isopropyl myristate | 18.0 |
| Glycerine mono stearate | 3.0 |
| Propylene glycol | 10.0 |
| Trans-4-guanidinomethylcyclohexanecarboxylic acid 2'-acetylphenylester hydrochloride | 20.0 |
| Caustic potash | 0.2 |
| Sodium hydrogensulfite | 0.01 |
| Antiseptic | q.s. |
| Perfume | q.s. |
| Ion exchanged water | balance |

Manufacturing Method

The preparation with respect to the present example was prepared by the same method described in the explanation of example 4.

| EXAMPLE 82 CREAM | weight % |
|---|---|
| Stearic acid | 6.0 |
| Sorbitane monostearate | 2.0 |
| Polyoxyethylene (20 moles) sorbitanemonostearate | 1.5 |
| Propylene glycol | 10.0 |
| Trans-4-guanidinomethylcyclohexanecarboxylic acid 2'-phenylphenylester hydrochloride | 7.0 |
| Glycerine trioctanoate | 10.0 |
| Squalene | 5.0 |
| Sodium hydrogensulfite | 0.01 |
| Ethylparaben | 0.3 |
| Perfume | q.s. |
| Ion exchanged water | balance |

Manufacturing Method

The preparation with respect to the present example was prepared by the same method described in the explanation of example 5.

| EXAMPLE 83 CREAM | weight % |
|---|---|
| Stearyl alcohol | 7.0 |
| Stearic acid | 2.0 |
| Hydrogenated lanoline | 2.0 |
| Squalane | 5.0 |
| 2-octyldodesylalcohol | 6.0 |
| Polyoxyethylene (25 moles) cetyl alcohol ether | 3.0 |
| Glycerinemonostearate | 2.0 |
| Propylene glycol | 5.0 |
| Trans-4-guanidinomethylcyclohexanecarboxylic acid 4'-chlorophenylester hydrochloride | 0.005 |
| Perfume | qs. |
| Sodium hydrogensulfite | 0.03 |
| Ethylparaben | 0.3 |
| Ion exchanged water | balance |

Manufacturing Method

The preparation with respect to the present example was prepared by the same method described in the explanation of example 6.

| EXAMPLE 84 MILKY LOTION | weight % |
|---|---|
| Stearic acid | 2.5 |
| Cetyl alcohol | 1.5 |
| Petrolatum | 5.0 |
| Liquid paraffin | 10.0 |
| Polyoxyethylene (10 moles) monoleate | 2.0 |
| Polyethylene glycol 1500 | 3.0 |
| Triethanolamine | 1.0 |
| Trans-4-guanidinomethylcyclohexanecarboxylic acid 4'-acetoaminophenylester hydrochloride | 10.0 |
| Sodium hydrogensulfite | 0.01 |
| Ethylparaben | 0.3 |
| Carboxyvinyl polymer | 0.05 |
| Perfume | q.s. |
| Ion exchanged water | balance |

Manufacturing Method

The preparation with respect to the present example was prepared by the same method described in the explanation of example 7.

| EXAMPLE 85 MILKY LOTION | weight % |
|---|---|
| Oil phase: | |
| Stearyl alcohol | 1.5 |
| Squalene | 2.0 |
| Petrolatum | 2.5 |
| Deodorized liquid lanoline | 1.5 |
| Evening primrose oil | 2.0 |
| Isopropyl myristate | 5.0 |
| Glycerine monoleate | 2.0 |
| Polyoxyethylene (60 moles) hydrogenated castor oil | 2.0 |
| Tocopherol acetate | 0.05 |
| Ethylparaben | 0.2 |
| Butylparaben | 0.1 |
| Trans-4-guanidinomethylcyclohexanecarboxylic acid 4'-sulfamoylphenylester hydrochloride | 1.0 |
| Trans-4-guanidinomethylcyclohexanecarboxylic acid 4'-benzoylphenylester hydrochloride | 1.0 |
| Perfume | q.s. |
| Aqueous phase: | |
| Sodium hydrogensulfite | 0.01 |
| Glycerol | 5.0 |
| Sodium hyaluronate | 0.01 |
| Carboxyvinyl polymer | 0.2 |
| Potassium hydroxide | 0.2 |
| Purified water | balance |

Manufacturing Method

The preparation with respect to the present example was prepared by the same method described in the explanation of example 8.

| EXAMPLE 86 JELLY | weight % |
|---|---|
| 95% ethyl alcohol | 10.0 |
| Dipropyleneglycol | 15.0 |
| Polyoxyethylene (50 moles) oleyl alcohol ether | 2.0 |
| Carboxyvinyl polymer | 1.0 |
| Caustic soda | 0.15 |
| L-arginine | 0.1 |
| Trans-4-guanidinomethylcyclohexanecarboxylic acid 2'-phenoxyphenylester hydrochloride | 1.0 |
| Trans-4-guanidinomethylcyclohexanecarboxylic acid 4'-formylphenylester hydrochloride | 1.0 |
| 4-hydroxybenzoic acid methylester | 0.2 |

41

-continued

| EXAMPLE 86 JELLY | weight % |
|---|---|
| Perfume | q.s. |
| Ion exchanged water | balance |

Manufacturing Method

The preparation with respect to the present example was prepared by the same method described in the explanation of example 9.

| EXAMPLE 87 LOTION | weight % |
|---|---|
| A phase: | |
| Ethanol (95%) | 10.0 |
| Polyoxyethylene (20 moles) octyldodecanol | 1.0 |
| 4-hydroxybenzoic acid methylester | 0.15 |
| Pantothenyl ethyl ether | 0.1 |
| Trans-4-guanidinomethylcyclohexanecarboxylic acid 2'-cyanophenylester hydrochloride | 0.05 |
| B Phase: | |
| Potassium hydroxide | 0.1 |
| C phase: | |
| Glycerol | 5.0 |
| Dipropyleneglycol | 10.0 |
| Sodium hydrogensulfite | 0.03 |
| Carboxyvinyl polymer | 0.2 |
| Purified water | balance |

Manufacturing Method

The preparation with respect to the present example was prepared by the same method described in the explanation of example 10.

| EXAMPLE 88 PACK | weight % |
|---|---|
| A phase: | |
| Dipropyleneglycol | 5.0 |
| Polyoxyethylene (60 moles) hydrogenated castor oil | 5.0 |
| B phase: | |
| Trans-4-guanidinomethylcyclohexanecarboxylic acid 4'-ethylphenylester hydrochloride | 1.0 |
| Trans-4-guanidinomethylcyclohexanecarboxylic acid 3',4'-dichlorophenylester hydrochloride | 1.0 |
| Olive oil | 5.0 |
| Tocopherol acetate | 0.2 |
| Ethylparaben | 0.2 |
| Perfume | 0.2 |
| C phase: | |
| Sodium hydrogensulfite | 0.03 |
| Polyvinyl alcohol (saponification degree 90, degree of polymerization 2000) | 13.0 |
| Ethanol | 7.0 |
| Purified water | balance |

Manufacturing Method

The preparation with respect to the present example was prepared by the same method described in the explanation of example 11.

COMPOUND GROUP 9

(1) Depigmentation Effect

The depigmentation effect of the compound group 9 was examined according to the method described above.

42

The result is shown in TABLE 17.

TABLE 17

| | COMPOUND | DEPIGMENTATION EFFECT |
|---|---|---|
| COMPARISON 1 | NONE | x |
| COMPARISON 2 | HYDROQUINONE | Δ |
| EXAMPLE 89 | Trans-4-benzylideneamino-methyl cyclohexanecarboxylic acid | ⊙ |
| EXAMPLE 90 | Trans-4-(3'-4'-dihydroxy-benzylideneaminomethyl) cyclohexanecarboxylic acid | ⊙ |
| EXAMPLE 91 | Trans-4-(4'-nitrobenzylidene-aminomethyl) cyclohexanecarboxylic acid | ⊙ |

As is clear from TABLE 17, the external preparation for the skin according to Examples 89 to 91 could also suppress deposition of melanoic pigment and suppress suntan.

(2) Skin Care Effect

The skin care effect of the compound group 9 was examined according to the method described above.

The result is shown in TABLE 18.

TABLE 18

| | drying of skin | wrinkle | drying of skin in morning |
|---|---|---|---|
| COMPARISON 1 | x | x | x |
| EXAMPLE 89 | ⊙ | ⊙ | ⊙ |
| EXAMPLE 90 | ⊙ | ⊙ | ⊙ |
| BXAMPLE 91 | ⊙ | ⊙ | ⊙ |

As is clear from TABLE 18, the external preparation for the skin according to Examples 89 to 91 had excellent skin care effect.

| EXAMPLE 92 CREAM | weight % |
|---|---|
| Stearic acid | 5.0 |
| Stearyl alcohol | 4.0 |
| Isopropyl myristate | 18.0 |
| Glycerine mono stearate | 3.0 |
| Propyleno glycol | 10.0 |
| Trans-4-(3',4',5'-trimethoxybenzylideneaminomethyl) cyclohexanecarboxylic acid | 20.0 |
| Caustic potash | 0.2 |
| Sodium hydrogensulfite | 0.01 |
| Antiseptic | q.s. |
| Perfume | q.s. |
| Ion exchanged water | balance |

Manufacturing Method

The preparation with respect to the present example was prepared by the same method described in the explanation of example 4.

| EXAMPLE 93 CREAM | weight % |
|---|---|
| Stearic acid | 6.0 |
| Sorbitane monostearate | 2.0 |
| Polyoxyethylene (20 moles) sorbitanemonostearate | 1.5 |
| Propylene glycol | 10.0 |
| Trans-4-(3'-pyridylmethylideneaminomethyl) cyclohexanecarboxylic acid | 7.0 |

| EXAMPLE 93 CREAM | weight % |
| --- | --- |
| Glycerine trioctanoate | 10.0 |
| Squalene | 5.0 |
| Sodium hydrogensulfite | 0.01 |
| Ethylparaben | 0.3 |
| Perfume | q.s. |
| Ion exchanged water | balance |

Manufacturing Method

The preparation with respect to the present example was prepared by the same method described in the explanation of example 5.

| EXAMPLE 94 CREAM | weight % |
| --- | --- |
| Stearyl alcohol | 7.0 |
| Stearic acid | 2.0 |
| Hydrogenated lanoline | 2.0 |
| Squalane | 5.0 |
| 2-octyldodesylalcohol | 6.0 |
| Polyoxyethylene (25 moles) cetyl alcohol ether | 3.0 |
| Glycerinemonostearate | 2.0 |
| Propylene glycol | 5.0 |
| Trans-4-(4'-isopropenylbenzylideneaminomethyl) cyclohexanecarboxylic acid | 0.005 |
| Perfume | q.s. |
| Sodium hydrogensulfite | 0.03 |
| Ethylparaben | 0.3 |
| Ion exchanged water | balance |

Manufacturing Method

The preparation with respect to the present example was prepared by the same method described in the explanation of example 6.

| EXAMPLE 95 MILKY LOTION | weight % |
| --- | --- |
| Stearic acid | 2.5 |
| Cetyl alcohol | 1.5 |
| Petrolatum | 5.0 |
| Liquid paraffin | 10.0 |
| Polyoxyethylene (10 moles) monooleate | 2.0 |
| Polyethylene glycol 1500 | 3.0 |
| Triethanolamine | 1.0 |
| Trans-4-(3',4'-dimethoxybenzylideneaminomethyl) cyclohexanecarboxylic acid | 10.0 |
| Sodium hydrogensulfite | 0.01 |
| Ethylparaben | 0.3 |
| Carboxyvinyl polymer | 0.05 |
| Perfume | q.s. |
| Ion exchanged water | balance |

Manufacturing Method

The preparation with respect to the present example was prepared by the same method described in the explanation of example 7.

| EXAMPLE 96 MILKY LOTION | weight % |
| --- | --- |
| Oil phase: | |
| Stearyl alcohol | 1.5 |
| Squalene | 2.0 |
| Petrolatum | 2.5 |

| EXAMPLE 96 MILKY LOTION | weight % |
| --- | --- |
| Deodorized liquid lanoline | 1.5 |
| Evening primrose oil | 2.0 |
| Isopropyl myristate | 5.0 |
| Glycerine monooleate | 2.0 |
| Polyoxyethylene (60 moles) hydrogenated castor oil | 2.0 |
| Tocopherol acetate | 0.05 |
| Ethylparaben | 0.2 |
| Butylparaben | 0.1 |
| Trans-4-(4'-chlorobenzylideneaminomethyl) cyclohexanecarboxylic acid | 1.0 |
| Trans-4-(2'-methoxybenzylideneaminomethyl) cyclohexanecarboxylic acid | 1.0 |
| Perfume | q.s. |
| Aqueous phase: | |
| Sodium hydrogensulfite | 0.01 |
| Glycerol | 5.0 |
| Sodium hyaluronate | 0.01 |
| Carboxyvinyl polymer | 0.2 |
| Potassium hydroxide | 0.2 |
| Purified water | balance |

Manufacturing Method

The preparation with respect to the present example was prepared by the same method described in the explanation of example 8.

| EXAMPLE 97 JELLY | weight % |
| --- | --- |
| 95% ethyl alcohol | 10.0 |
| Dipropyleneglycol | 15.0 |
| Polyoxyethylene (50 moles) oleyl alcohol ether | 2.0 |
| Carboxyvinyl polymer | 1.0 |
| Caustic soda | 0.15 |
| L-arginine | 0.1 |
| Trans-4-(2'-hydroxybenzylideneaminomethyl) cyclohexanecarboxylic acid | 1.0 |
| Trans-4-(3'-trifluoromethylbenzylideneaminomethyl) cyclohexanecarboxylic acid | 1.0 |
| 4-hydroxybenzoic acid methylester | 0.2 |
| Perfume | q.s. |
| Ion exchanged water | balance |

Manufacturing Method

The preparation with respect to the present example was prepared by the same method described in the explanation of example 9.

| EXAMPLE 98 LOTION | weight % |
| --- | --- |
| A phase: | |
| Ethanol (95%) | 10.0 |
| Polyoxyethylene (20 moles) octyldodecanol | 1.0 |
| 4-hydroxybenzoic acid methylester | 0.15 |
| Pantothenyl ethyl ether | 0.1 |
| Trans-4-(3'-carboxy-4'-hydroxybenzylideneaminomethyl) cyclohexanecarboxylic acid | 0.05 |
| B phase: | 0.1 |
| Potassium hydroxide | |
| C phase: | |
| Glycerol | 5.0 |
| dipropyleneglycol | 10.0 |
| Sodium hydrogensulfite | 0.03 |
| Carboxyvinyl polymer | 0.2 |
| Purified water | balance |

Manufacturing Method

The preparation with respect to the present example was prepared by the same method described in the explanation of example 10.

| EXAMPLE 99 PACK | weight % |
|---|---|
| A phase: | |
| Dipropyleneglycol | 5.0 |
| Polyxoyethylene (60 moles) hydrogenated castor oil | 5.0 |
| B phase: | |
| Trans-4-(2'-nitrobenzylideneaminomethyl) cyclohexanecarboxylic acid | 1.0 |
| Trans-4-(3',4'-dihydroxybenzylideneaminomethyl) cyclohexanecarboxylic acid ethyl ester | 1.0 |
| Olive oil | 5.0 |
| Tocopherol acetate | 0.2 |
| Ethylparaben | 0.2 |
| Perfume | 0.2 |
| C phase: | |
| Sodium hydrogensulfite | 0.03 |
| Polyvinyl alcohol (saponification degree 90, degree of polymerixation 2000) | 13.0 |
| Ethanol | 7.0 |
| Purified water | balance |

Manufacturing Method

The preparation with respect to the present example was prepared by the same method described in the explanation of example 11.

As is clear from the above-described examples, the external preparation for the skin including derivatives of tranexamic acid, have excellent whitening effect as well as skin care effect.

What is claimed is:

1. A composition for skin depigmentation comprising amide derivatives of tranexamic acid and salts thereof represented by the following formula B:

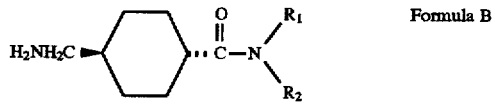

Formula B in the formula B, $R_1$ and $R_2$ are the same or different and represent hydrogen, straight or branched allyl group having 1 to 18 carbon atoms, cycloalkyl group having 5–8 carbon atoms, benzyl group or having the structure in the following formula C:

Formula C in the formula C, X represents lower alkyl group, lower alkoxy group atoms, hydroxy group, amino group or halogen atom, and n=0–3.

2. A composition for skin depigmentation comprising amide derivatives and the salt derivatives thereof represented by the following formula D:

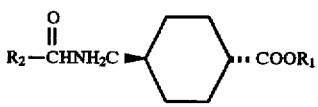

Formula D in the formula D, $R_1$ represents a hydrogen or a lower alkyl group having 1 to 4 carbon atoms, $R_2$ represents an alkyl group having 1 to 17 carbon atoms, a cycloalkyl group having 5 to 11 carbon atoms, an alkenyl group having 3 to 17 carbon atoms, a pyridyl group, a trifluoromethyl group, or the following formula E:

Formula E in the formula E, X and Y represent hydroxy group, methoxy group, amino group or halogen atom respectively, m=0–3, n=0–3 or the following formula F:

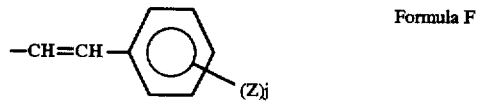

Formula F in the formula F, Z represents a hydroxy group or methoxy group, and j=0–3.

3. A composition for skin depigmentation comprising compounds and salts thereof represented by the following formula G:

Formula G in the formula G, R represents an amino acid residue, in which a carbon atom in a carboxyl group bonds to a nitrogen of the tranexamic acid by an amide bond, which is selected from the group consisting of L-flycyl, L-seryl, L-threonyl, L-cysteinyl, L-tyrosyl, L-asparaginyl, L-qlutaminyl, L-alanyl, L-valyl, L-leucyl, L-isoleucyl, L-prolyl, L-phenylalanyl, L-tryptophanyl, L-methionyl, L-α-aspartyl, L-α-glutamyl, L-lysyl, L-arginyl, L-histidyl, and L-ornithyl group.

4. A composition for skin depigmentation comprising compounds and salts thereof represented by the following formula I:

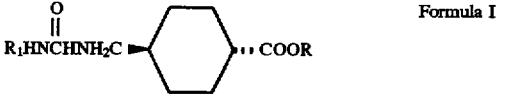

Formula I in the formula I, R represents a hydrogen or a lower alkyl group having 1 to 8 carbon atoms, $R_1$ represents a hydrogen, an alkyl group having 1 to 8 carbon atoms, cyclohexyl group, an aryl group, or $(CH_2)COOCH_2CH_3$.

5. A composition for skin depigmentation comprising trans-4-guanidinomethylcyclo hexanecarboxylic acid derivatives and salts thereof represented by the following formula K:

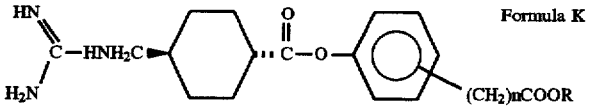

Formula K in the formula K, R represents hydrogen, a lower alkyl group, a benzyl group, or a phenyl group, and n=0–2.

6. A composition for skin depigmentation comprising cyclohexanecarboxylic acid derivatives and salts thereof represented by the following formula M:

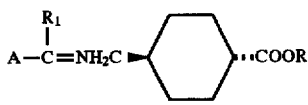

Formula M in the formula M, A represents a phenyl group, a pyridyl group, a p-isopropenylphenyl group or a group represented by the following formula N:

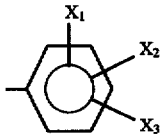

Formula N in the formula N, $X_1$ represents hydrogen, a hydroxy group or a methoxy group, $X_2$ represents hydrogen, a hydroxy group or a methoxy group, $X_3$ represents a hydroxy group, a methoxy group, a halogen atom, a nitro group, a trifluoromethyl group, a carboxyl group or the following formula O:

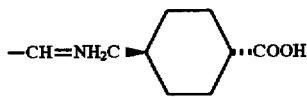

Formula O

R represents a hydrogen atom, Na or the alkyl group having 1~4 of carbon atoms, $R_1$ represents a hydrogen atom or an alkyl group having 1~10 carbon atoms.

7. The composition of claim 2, wherein the amide derivative is one or more derivatives selected from the group consisting of Trans-4-(trans-4'-isobutylcyclohexylcarbonylaminomethyl) cyclohexanecarboxylic acid, Trans-4-oleoylaminomethyl)cyclohexane carboxylic acid, Trans-4-(3',4'-dimethoxycinnamoylminomethyl)cyclohexanecarboxylic acid, and the salts thereof.

8. The composition of claim 3, wherein the amino acid residue is selected from the group consisting of L-alanyl, L-valyl, and L-threonyl.

9. The composition of claim 4, wherein R is hydrogen and $R_1$ is selected from hydrogen atom, ethyl group, and cyclohexyl group.

10. The composition of claim 2, wherein $R_1$ is hydrogen atom and $R_2$ is selected from the group consisting of methyl group and a group represented by the following formula P.

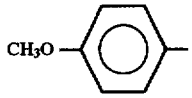

Formula P

* * * * *